US012626361B2

(12) United States Patent
Takahashi et al.

(10) Patent No.: US 12,626,361 B2
(45) Date of Patent: May 12, 2026

(54) RECORDING MEDIUM, INFORMATION PROCESSING APPARATUS, INFORMATION PROCESSING SYSTEM, AND INFORMATION PROCESSING METHOD

(71) Applicant: Konica Minolta, Inc., Tokyo (JP)

(72) Inventors: Hidekazu Takahashi, Toyonaka (JP); Hisashi Wada, Tokyo (JP); Kei Okabayashi, Yokohama (JP)

(73) Assignee: Konica Minolta, Inc., Tokyo (JP)

( * ) Notice: Subject to any disclaimer, the term of this patent is extended or adjusted under 35 U.S.C. 154(b) by 350 days.

(21) Appl. No.: 18/333,774

(22) Filed: Jun. 13, 2023

(65) Prior Publication Data

US 2023/0401708 A1     Dec. 14, 2023

(30) Foreign Application Priority Data

Jun. 14, 2022     (JP) ................................. 2022-095661

(51) Int. Cl.
| | |
|---|---|
| *G06T 7/00* | (2017.01) |
| *G06F 3/04812* | (2022.01) |
| *G16H 30/40* | (2018.01) |

(52) U.S. Cl.
CPC ........ *G06T 7/0012* (2013.01); *G06F 3/04812* (2013.01); *G16H 30/40* (2018.01);
(Continued)

(58) Field of Classification Search
CPC .................................................. G06T 7/0012
See application file for complete search history.

(56) References Cited

U.S. PATENT DOCUMENTS

| | | | |
|---|---|---|---|
| 2022/0079430 A1* | 3/2022 | Wang ...................... | G06N 20/10 |
| 2023/0154619 A1* | 5/2023 | Hirata ................... | A61B 6/037 |
| | | | 382/128 |

FOREIGN PATENT DOCUMENTS

| | | |
|---|---|---|
| JP | 2004-344232 A | 12/2004 |
| JP | 2005-102862 A | 4/2005 |

(Continued)

OTHER PUBLICATIONS

Notice of Reasons for Refusal issued in related Japanese Application No. 2022-095661 mailed Aug. 20, 2024 (12 pages).

*Primary Examiner* — Di Xiao
(74) *Attorney, Agent, or Firm* — Osha Bergman Watanabe & Burton LLP

(57) ABSTRACT

A non-transitory computer-readable recording medium storing instructions causing a computer to execute: acquiring information on whether each of one or more first lesion detection regions is false positive, the one or more first lesion detection regions being input by a user with respect to a first analysis result and obtained by computer processing on a first medical image of a patient; acquiring a second analysis result including one or more second lesion detection regions that are obtained by computer processing on a second medical image of the patient; and displaying a false correspondence region in a different manner from a manner of displaying a non-false correspondence region. The false correspondence region corresponds to a first lesion detection region indicated as being false positive, and the non-false correspondence region corresponds to a first lesion detection region indicated as being not false positive, in the acquired information.

24 Claims, 13 Drawing Sheets

(52) U.S. Cl.
CPC ............... *G06T 2207/20104* (2013.01); *G06T
2207/30096* (2013.01)

(56)                    References Cited

FOREIGN PATENT DOCUMENTS

| | | | |
|---|---|---|---|
| JP | 2005-328977 | A | 12/2005 |
| JP | 2005-334219 | A | 12/2005 |
| JP | 4651353 | B2 | 3/2011 |
| JP | 2016-157291 | A | 9/2016 |
| WO | 2022/031945 | A1 | 2/2022 |

* cited by examiner

100

10
MEDICAL IMAGE MANAGEMENT SERVER

20
MODALITY

20
MODALITY

· · ·

N

30
INFORMATION PROCESSING APPARATUS

10

MEDICAL IMAGE MANAGEMENT SERVER

11
CONTROLLER

14
STORAGE SECTION

141
USER MANAGEMENT TABLE

142
DATA MANAGEMENT TABLE

143
MEDICAL IMAGE STORAGE AREA

144
ANALYSIS RESULT STORAGE AREA

145
IMAGE INTERPRETATION RESULT STORAGE AREA

12
COMMUNICATION SECTION

13
IMAGE ANALYSIS SECTION

15

| IMAGE ID | PATIENT ID | IMAGING DATE AND TIME | MODALITY | SITE | DIRECTION | ... | ANALYSIS RESULT ID | IMAGE INTERPRETATION RESULT ID |
|---|---|---|---|---|---|---|---|---|
|  |  |  |  |  |  |  |  |  |
|  |  |  |  |  |  |  |  |  |
|  |  |  |  |  |  |  |  |  |
|  |  |  |  |  |  |  |  |  |
|  |  |  |  |  |  |  |  |  |

142

30

INFORMATION PROCESSING APPARATUS

CONTROLLER 31

OPERATION PART 32

COMMUNICATION SECTION 34

DISPLAY PART 33

STORAGE SECTION 35

IMAGE INTERPRETATION SUPPORT PROCESSING PROGRAM

Figure 5:
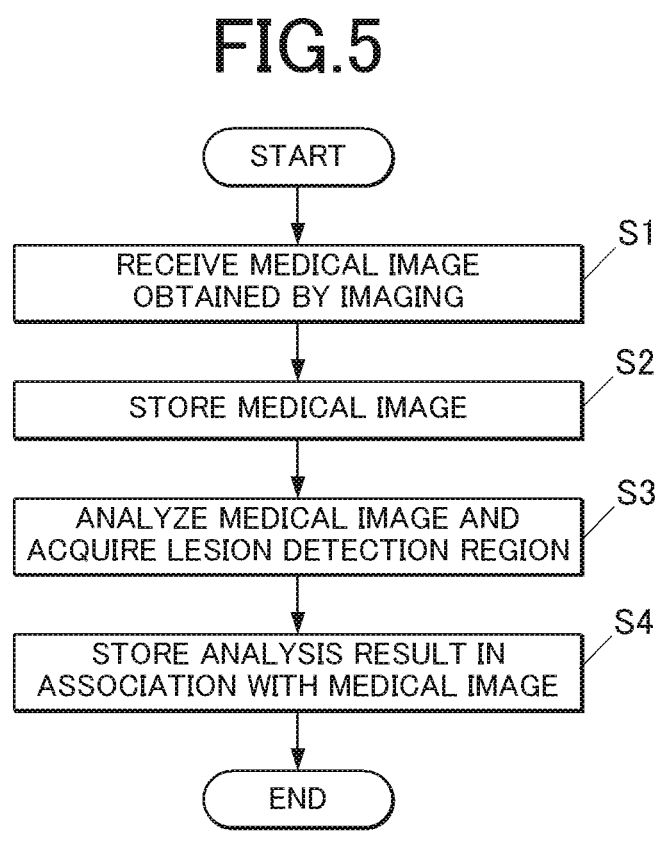

START

RECEIVE MEDICAL IMAGE
OBTAINED BY IMAGING          S1

STORE MEDICAL IMAGE          S2

ANALYZE MEDICAL IMAGE AND
ACQUIRE LESION DETECTION REGION          S3

STORE ANALYSIS RESULT IN
ASSOCIATION WITH MEDICAL IMAGE          S4

END

FIG.8

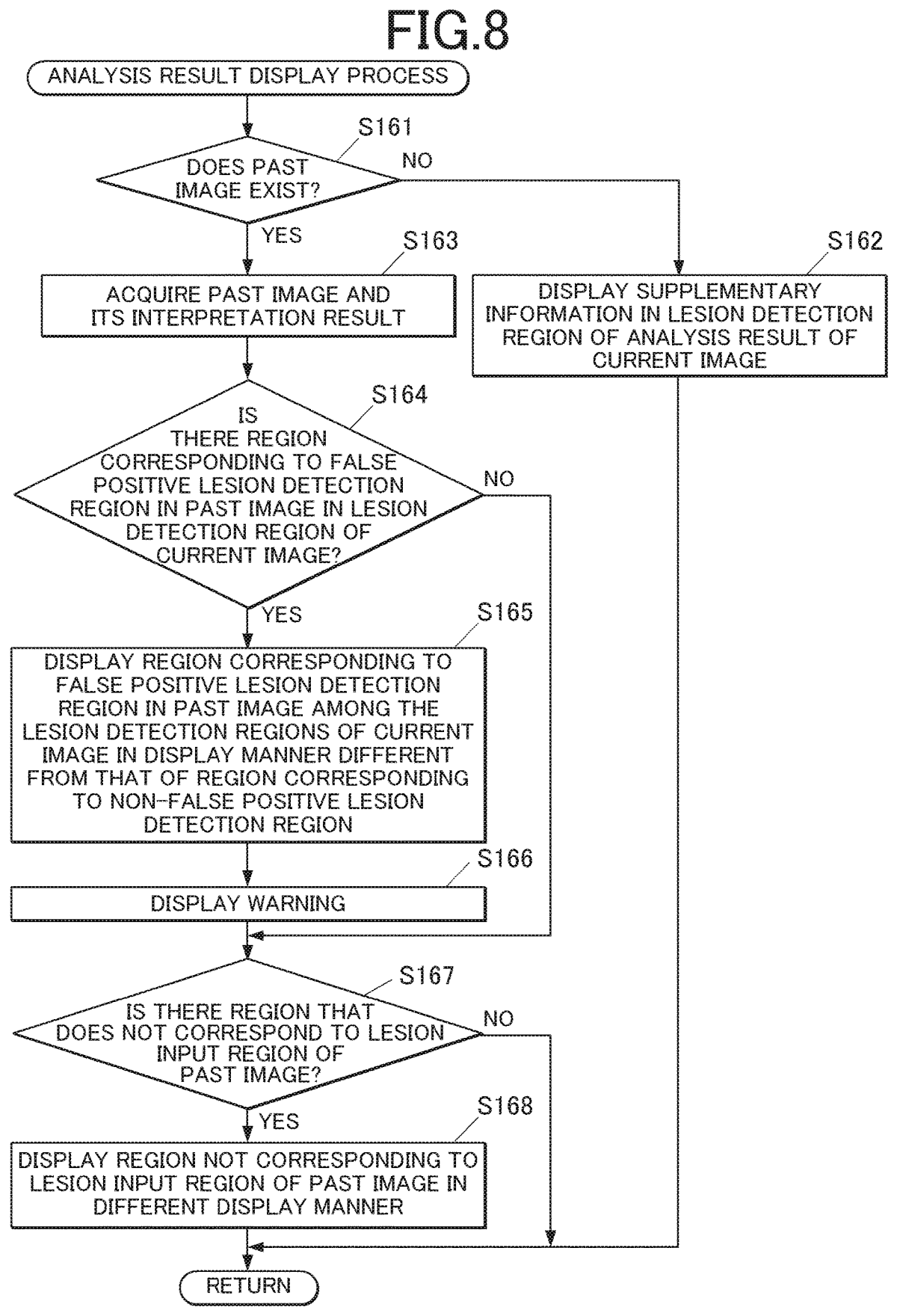

```
        ┌──────────────────────────────────┐
        │  ANALYSIS RESULT DISPLAY PROCESS  │
        └──────────────────────────────────┘
                        │
                        ▼           S161
              ╱───────────────╲        NO
             ╱   DOES PAST      ╲───────────────────────────┐
             ╲  IMAGE EXIST?    ╱                            │
              ╲───────────────╱                              │
                    │ YES                                    │
                    │            S163              S162       ▼
        ┌───────────────────────────┐   ┌──────────────────────────────┐
        │  ACQUIRE PAST IMAGE AND    │   │   DISPLAY SUPPLEMENTARY       │
        │  ITS INTERPRETATION RESULT │   │ INFORMATION IN LESION DETECTION│
        └───────────────────────────┘   │  REGION OF ANALYSIS RESULT OF │
                    │                    │        CURRENT IMAGE          │
                    ▼          S164      └──────────────────────────────┘
              ╱─────────────╲                            │
             ╱      IS         ╲                          │
            ╱  THERE REGION      ╲                        │
           ╱ CORRESPONDING TO FALSE╲        NO            │
          ╱ POSITIVE LESION DETECTION╲──────────────┐     │
          ╲ REGION IN PAST IMAGE IN LESION╱          │     │
           ╲ DETECTION REGION OF        ╱            │     │
            ╲    CURRENT IMAGE?       ╱              │     │
              ╲─────────────╱                        │     │
                    │ YES         S165                │     │
        ┌───────────────────────────────┐            │     │
        │  DISPLAY REGION CORRESPONDING TO│           │     │
        │   FALSE POSITIVE LESION DETECTION│          │     │
        │   REGION IN PAST IMAGE AMONG THE │          │     │
        │ LESION DETECTION REGIONS OF CURRENT│        │     │
        │  IMAGE IN DISPLAY MANNER DIFFERENT │        │     │
        │ FROM THAT OF REGION CORRESPONDING  │        │     │
        │   TO NON-FALSE POSITIVE LESION     │        │     │
        │         DETECTION REGION           │        │     │
        └───────────────────────────────┘            │     │
                    │              S166                │     │
        ┌───────────────────────────┐                 │     │
        │      DISPLAY WARNING       │                 │     │
        └───────────────────────────┘                 │     │
                    │◄────────────────────────────────┘     │
                    ▼            S167                        │
              ╱───────────────╲                             │
             ╱  IS THERE REGION THAT╲       NO               │
            ╱ DOES NOT CORRESPOND TO LESION╲────────────┐    │
            ╲    INPUT REGION OF        ╱                │    │
             ╲     PAST IMAGE?        ╱                  │    │
              ╲───────────────╱                          │    │
                    │ YES        S168                     │    │
        ┌───────────────────────────────┐                │    │
        │ DISPLAY REGION NOT CORRESPONDING TO│            │    │
        │ LESION INPUT REGION OF PAST IMAGE IN│           │    │
        │      DIFFERENT DISPLAY MANNER      │            │    │
        └───────────────────────────────┘                │    │
                    │◄───────────────────────────────────┘    │
                    │◄──────────────────────────────────────────┘
                    ▼
              ┌──────────┐
              │  RETURN  │
              └──────────┘
```

Figure 11:
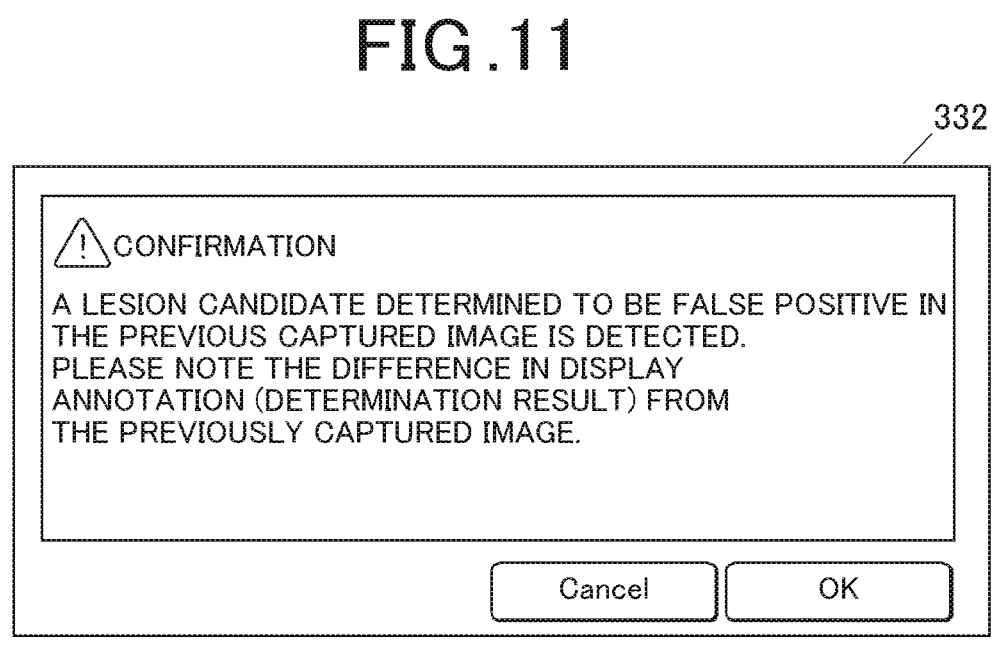

⚠CONFIRMATION

A LESION CANDIDATE DETERMINED TO BE FALSE POSITIVE IN
THE PREVIOUS CAPTURED IMAGE IS DETECTED.
PLEASE NOTE THE DIFFERENCE IN DISPLAY
ANNOTATION (DETERMINATION RESULT) FROM
THE PREVIOUSLY CAPTURED IMAGE.

Cancel          OK

RECORDING MEDIUM, INFORMATION PROCESSING APPARATUS, INFORMATION PROCESSING SYSTEM, AND INFORMATION PROCESSING METHOD

CROSS-REFERENCE TO RELATED APPLICATIONS

The entire disclosure of Japanese Patent Application No. 2022-095661 filed on Jun. 14, 2022 is incorporated herein by reference.

BACKGROUND

Technical Field

The present invention relates to a recording medium, an information processing apparatus, an information processing system, and an information processing method.

Description of Related Art

In recent years, a diagnosis support (CAD: Computer Aided Detection/Diagnosis) system has been put into practical use in which a medical image is analyzed using a computer, a lesion detection region detected by the image analysis is presented to a doctor, and the doctor is asked to make a determination.

For example, Japanese Patent No. 4651353 discloses that an annotation is added to a lesion detection region detected by CAD.

Recently, a system capable of detecting a lesion candidate region in an image by performing computer processing such as ArtificialIntelligence (AI) analysis based on machine learning or a deep learning technique on a medical image has also been proposed.

There are many false positives in a lesion detection region detected by computer processing such as CAD and AI. Therefore, a doctor determines whether or not the lesion detection region detected by the computer is false positive.

However, when the computer detects a lesion in a new image of the same patient, the computer may also detect and display a region corresponding to a lesion detection region determined to be false positive in the previous image by the doctor as a lesion detection region.

Therefore, for example, a skilled case of a skilled doctor or a doctor who has interpreted last time, since false positive result is displayed again, the doctor may feel annoyed. Furthermore, in a case of an unskilled doctor or a doctor who has not interpreted last time, there is also a risk that false positive will be overlooked.

SUMMARY

One or more embodiments of the present invention provide a technological improvement over such conventional technologies as discussed above. In particular, one or more embodiments of the present invention provide a recording medium, an information processing apparatus, an information processing system, and an information processing method that enable a user to recognize false positive region among lesion detection regions obtained by computer processing. This provides a practical, technological improvement over conventional technologies that would be readily appreciated by those skilled in the art, as will be discussed in further detail later.

According to an aspect of the present invention, there is provided a non-transitory computer-readable recording medium storing instructions causing a computer to execute: first acquiring that is acquiring information on whether each of a lesion detection region (i.e., one or more first lesion detection regions) input by a user with respect to a first analysis result including at least one lesion detection region obtained by computer processing on a first medical image of a patient is false positive; second acquiring that is acquiring a second analysis result including at least one lesion detection region (i.e., one or more second lesion detection regions) obtained by computer processing on a second medical image of the patient; and displaying that is displaying a first region (i.e., false correspondence region) among the lesion detection region obtained by the second acquiring in a display manner different from a display manner of a second region (i.e., non-false correspondence region), the first region being a region corresponding to a lesion detection region included in the first analysis result for which information indicating that the lesion detection region is false positive is acquired by the first acquiring, and the second region being a region corresponding to a lesion detection region included in the first analysis result for which information indicating that the lesion detection region is not false positive is acquired by the first acquiring.

According to an aspect of the present invention, there is provided an information processing apparatus comprising a hardware processor that: acquires information on whether each of a lesion detection region (i.e., one or more first lesion detection regions) input by a user with respect to a first analysis result including at least one lesion detection region obtained by computer processing on a first medical image of a patient is false positive; acquires a second analysis result including at least one lesion detection region (i.e., one or more second lesion detection regions) obtained by computer processing on a second medical image of the patient; and displays a first region (i.e., false correspondence region) among the lesion detection region included in the second analysis result in a display manner different from a display manner of a second region (i.e., non-false correspondence region), the first region being a region corresponding to a lesion detection region included in the first analysis result for which information indicating that the lesion detection region is false positive is acquired, and the second region being a region corresponding to a lesion detection region included in the first analysis result for which information indicating that the lesion detection region is not false positive is acquired.

According to an aspect of the present invention, there is provided an information processing system comprising a hardware processor that: acquires information on whether each of a lesion detection region (i.e., one or more first lesion detection regions) input by a user with respect to a first analysis result including at least one lesion detection region obtained by computer processing on a first medical image of a patient is false positive; acquires a second analysis result including at least one lesion detection region (i.e., one or more second lesion detection regions) obtained by computer processing on a second medical image of the patient; and displays a first region (i.e., false correspondence region) among the lesion detection region included in the second analysis result in a display manner different from a display manner of a second region (i.e., non-false correspondence region), the first region being a region corresponding to a lesion detection region included in the first analysis result for which information indicating that the lesion detection region is false positive is acquired, and the second region being a region corresponding to a lesion detection region included in the first analysis result for which information indicating that the lesion detection region is not false positive is acquired.

According to an aspect of the present invention, there is provided an information processing method comprising: first acquiring that is acquiring information on whether each of a lesion detection region (i.e., one or more first lesion detection regions) input by a user with respect to a first analysis result including at least one lesion detection region obtained by computer processing on a first medical image of a patient is false positive; second acquiring that is acquiring a second analysis result including at least one lesion detection region (i.e., one or more second lesion detection regions) obtained by computer processing on a second medical image of the patient; and displaying that is displaying a first region (i.e., false correspondence region) among the lesion detection region obtained by the second acquiring in a display manner different from a display manner of a second region (i.e., non-false correspondence region), the first region being a region corresponding to a lesion detection region included in the first analysis result for which information indicating that the lesion detection region is false positive is acquired by the first acquiring, and the second region being a region corresponding to a lesion detection region included in the first analysis result for which information indicating that the lesion detection region is not false positive is acquired by the first acquiring.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 5 is a flowchart illustrating medical image analysis processing executed by a medical image management server;

FIG. 8 is a flowchart illustrating the analysis result display process executed in step S16 of FIG. 6;

FIG. 11 is a diagram showing a display example (display of a pop-up screen) for notifying the user that a region corresponding to a region registered as false positive in the past image is included in the lesion detection region of the analysis result of the current image;

DETAILED DESCRIPTION

Embodiments of a recording medium storing instructions, an information processing apparatus, an information processing system, and an information processing method will be described below. However, the scope of the invention is not limited to the disclosed embodiments.

[Configuration of Medical Image Display System]

Figure 1:
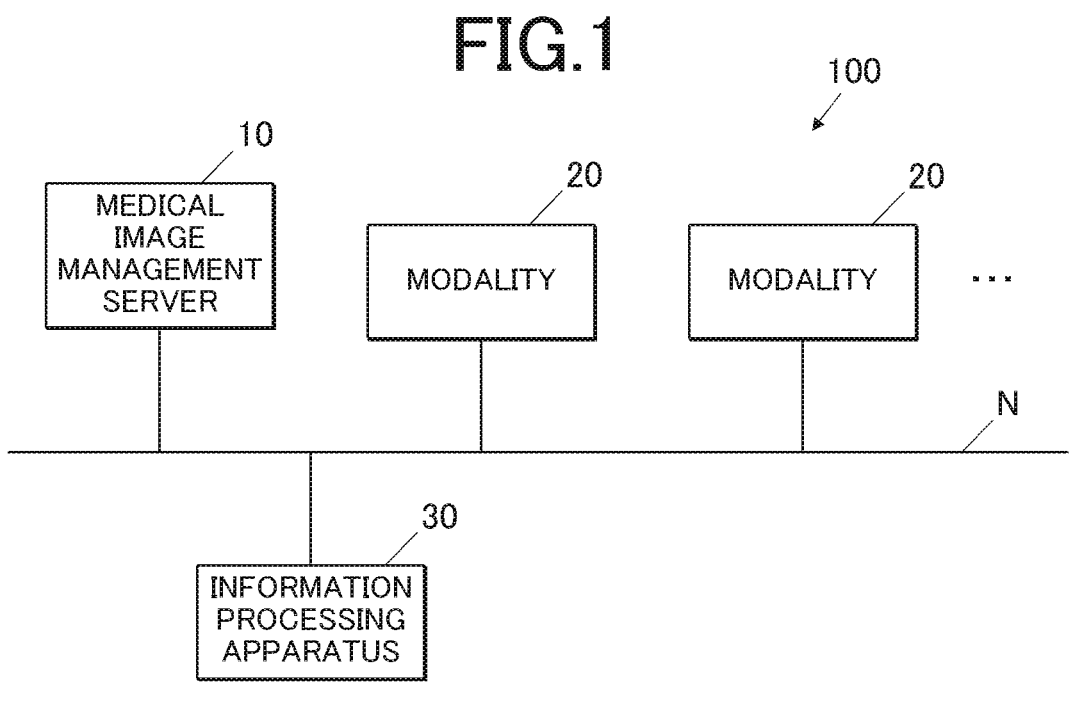
FIG. 1 is a view of a system configuration of a medical image display system.

FIG. 1 shows a system configuration of a medical image display system 100 as an information processing system.

As illustrated in FIG. 1, the medical image display system 100 includes a medical image management server 10, modalities 20, 20, . . . , and an information processing apparatus 30. Each apparatus constituting the medical image display system 100 can perform data communication via a communication network N. Note that the information processing apparatus 30 may be connectable to the medical image management server 10 via the communication network N as necessary. In the medical image display system 100, medical images and analysis results stored in the medical image management server 10 can be displayed on the information processing apparatus 30. Each device constituting the medical image display system 100 conforms to the HL7 (Health Level Seven) standard or the DICOM (Digital Image and Communications in Medicine) standard. Communication between the apparatuses is performed in accordance with HL7 or DICOM. Note that the number of information processing apparatuses 30 is not particularly limited.

The modality 20 performs imaging of a patient (subject) and generates image data of a medical image. As the modality 20, for example, computed radiography (CR), digital radiography (DR), computed tomography (CT), magnetic resonance imaging (MRI), ultra sonography (US), nuclear medicine (NM), endoscope (ES), or the like is used.

Furthermore, the modality 20 attaches, to a medical image, image attribute information on the medical image. The image attribute information includes a patient ID, a patient name, a date of birth, a sex, an imaging date and time, an image ID, a modality, a site, a direction, and the like.

The image data of the medical image generated by the modality 20 is transmitted to the medical image management server 10.

The medical image management server 10 stores and manages image data of a medical image generated by the modality 20. Examples of the medical image management server 10 include a picture archiving and communication system (PACS).

The information processing apparatus 30 is a computer apparatus such as a personal computer (PC) or a tablet. The information processing apparatus 30 is used when a user such as a doctor reads a medical image.

[Configuration of Medical Image Management Server]

Figure 2:
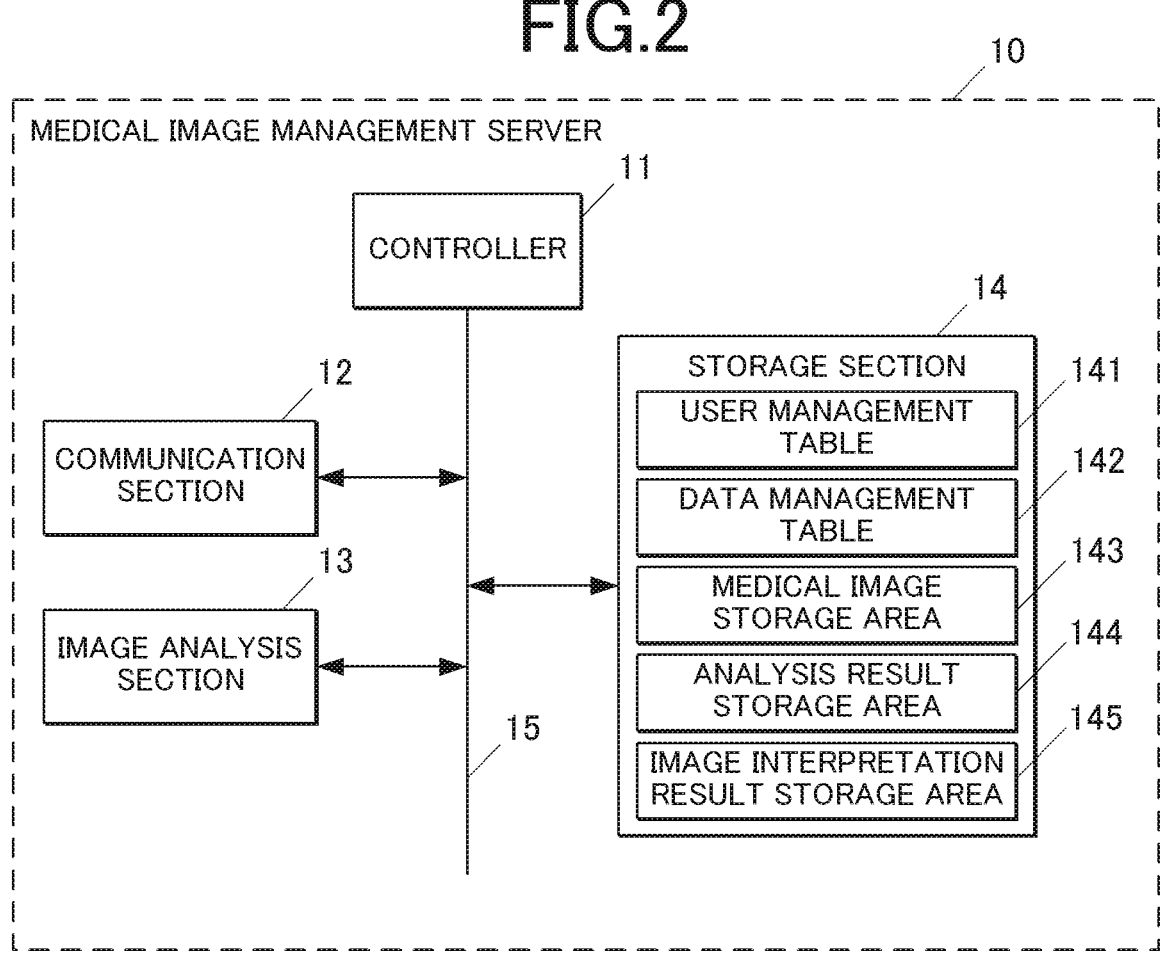
FIG. 2 is a block diagram showing a functional configuration of the medical image management server.

FIG. 2 illustrates a functional configuration of the medical image management server 10. The medical image management server 10 includes a controller 11, a communication section (or communication interface) 12, an image analysis section 13, a storage section (or storage) 14, and the like. These components of the medical image management server 10 are connected to each other by a bus 15.

The controller 11 includes a central processing unit (CPU), a random access memory (RAM), and the like. The controller 11 comprehensively controls processing operation of each section of the medical image management server 10. Specifically, the controller 11 reads various processing programs or instructions stored in the storage section 14, develops the programs or instructions in a RAM, and performs various kinds of processing in cooperation with the programs or instructions.

The communication section 12 includes a network interface and the like. The communication section 12 transmits and receives data to and from an external device connected through the communication network N. For example, the communication section 12 receives a medical image obtained by imaging a patient with the modality 20. Further, the communication section 12 transmits a medical image and an analysis result requested from the information processing apparatus 30 to the information processing apparatus 30.

The image analysis section 13 performs computer processing on a medical image obtained by imaging a patient, and generates data of an analysis result. As the computer processing, for example, AI analysis using AI (Artificial Intelligence) including detection of a lesion candidate by CAD (Computer Aided Diagnosis) is used. The data of the analysis result includes, for example, grayscale softcopy presentation state (GSPS) data of DICOM, overlay data, and the like. The data of the analysis result includes an analysis result ID for identifying the analysis result and information on the detected lesion detection region. The information on the lesion detection region includes the position of the detected lesion, the type of lesion, the content of supplementary information (annotation information), and the like.

The image analysis section 13 is realized by software processing by cooperation of the program or instructions stored in the storage section 14 and the CPU of the controller 11.

The storage section 14 is configured of a hard disk drive (HDD), a non-volatile semiconductor memory, or the like. The storage section 14 stores various processing programs or instructions, parameters and files required for execution of the programs or instructions, and the like.

Furthermore, the storage section 14 stores a user management table 141 and a data management table 142. The storage section 14 includes a medical image storage area 143, an analysis result storage area 144, and an image interpretation result storage area 145.

The user management table 141 is a table for managing information on a user who uses the medical image display system 100. The user is a medical worker such as a doctor. The user management table 141 stores, for each user, a user ID, a password, a name, an affiliation, an e-mail address, a telephone number, and the like in association with each other.

The user ID is identification information on a user. The password is used for authentication when a user accesses the medical image management server 10 from the information processing apparatus 30. The name is a name of the user. The affiliation is information of a medical facility, a department, or the like to which the user belongs. The e-mail address is an e-mail address of the user. The telephone number is a telephone number of the user.

The data management table 142 is a table for managing data in the medical image management server 10.

Figure 3:
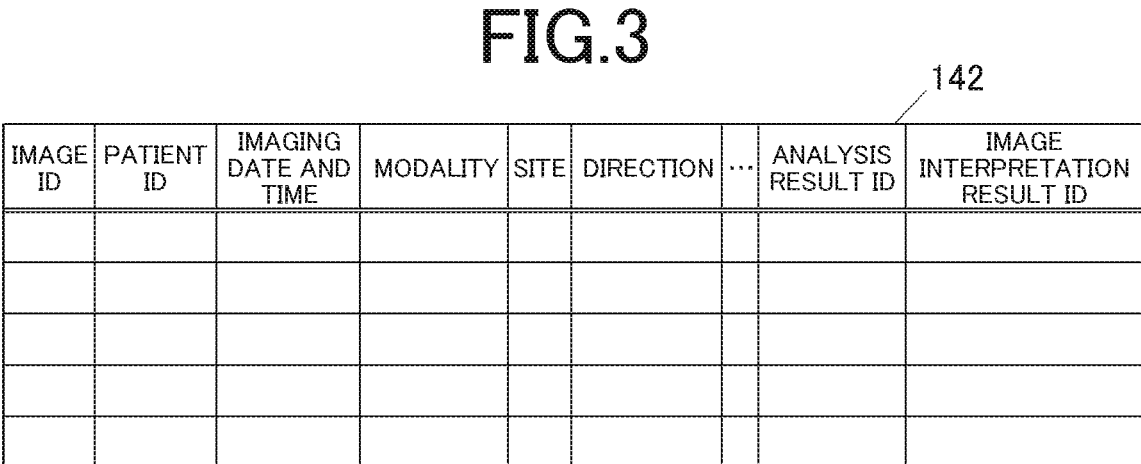
FIG. 3 is a diagram illustrating a data configuration of a data management table.

FIG. 3 shows a data configuration of the data management table 142. The data management table 142 stores, for each medical image stored in the medical image storage area 143, an image ID, a patient ID, an imaging date and time, a modality, a site, a direction, an analysis result ID, an image interpretation result ID, and the like in association with each other.

The image ID is identification information of a medical image. The patient ID is identification information on a patient who is an imaging target of a medical image. The imaging date and time is date and time when the medical image is imaged. The modality is a modality in which a medical image is captured. The site is a site that is an imaging target of a medical image. The direction is an imaging direction of the medical image. The analysis result ID is identification information of the analysis result obtained by analyzing the medical image by the image analysis section 13. The image interpretation result ID is identification information for identifying the interpretation result of the medical image by the user (doctor).

The medical image storage area 143 stores image data of a medical image received from the modality 20.

Data of an analysis result for the medical image by computer processing is stored in the analysis result storage area 144.

The image interpretation result storage area 145 stores data of the interpretation result for the medical image by the doctor who is the user. The image interpretation result includes an image interpretation result ID, information on the lesion input region input by the user, and information on whether or not each of the lesion detection regions included in the analysis result by computer processing input by the user is false positive. The information on the lesion input region includes the position of the lesion input region, the type of lesion, the content of supplementary information, and the like. In addition, the information on whether or not each of the lesion detection regions included in the analysis result by the computer processing is false positive includes position information of each lesion detection region in the analysis result.

Upon receiving a medical image from the modality 20 via the communication section 12, the controller 11 causes the storage section 14 to store the medical image. Further, the controller 11 causes the image analysis section 13 to analyze the received medical image.

When there is an acquisition request for a medical image and an analysis result from the information processing apparatus 30 via the communication section 12, the controller 11 reads the medical image and the analysis result from the storage section 14, and provides the read medical image to the information processing apparatus 30 via the communication section 12.

In a case where there is an acquisition request for the past image and the interpretation result for the acquired medical image from the information processing apparatus 30 via the communication section 12, the controller 11 reads the past image and the interpretation result thereof from the storage section 14 and provides the read medical image to the information processing apparatus 30 via the communication section 12. Here, the past image is an image of the same site (direction) of the same patient as the medical image acquired by the information processing apparatus 30, and is an image captured on a different date and time from the medical image.

[Configuration of Information Processing Apparatus]

Figure 4:
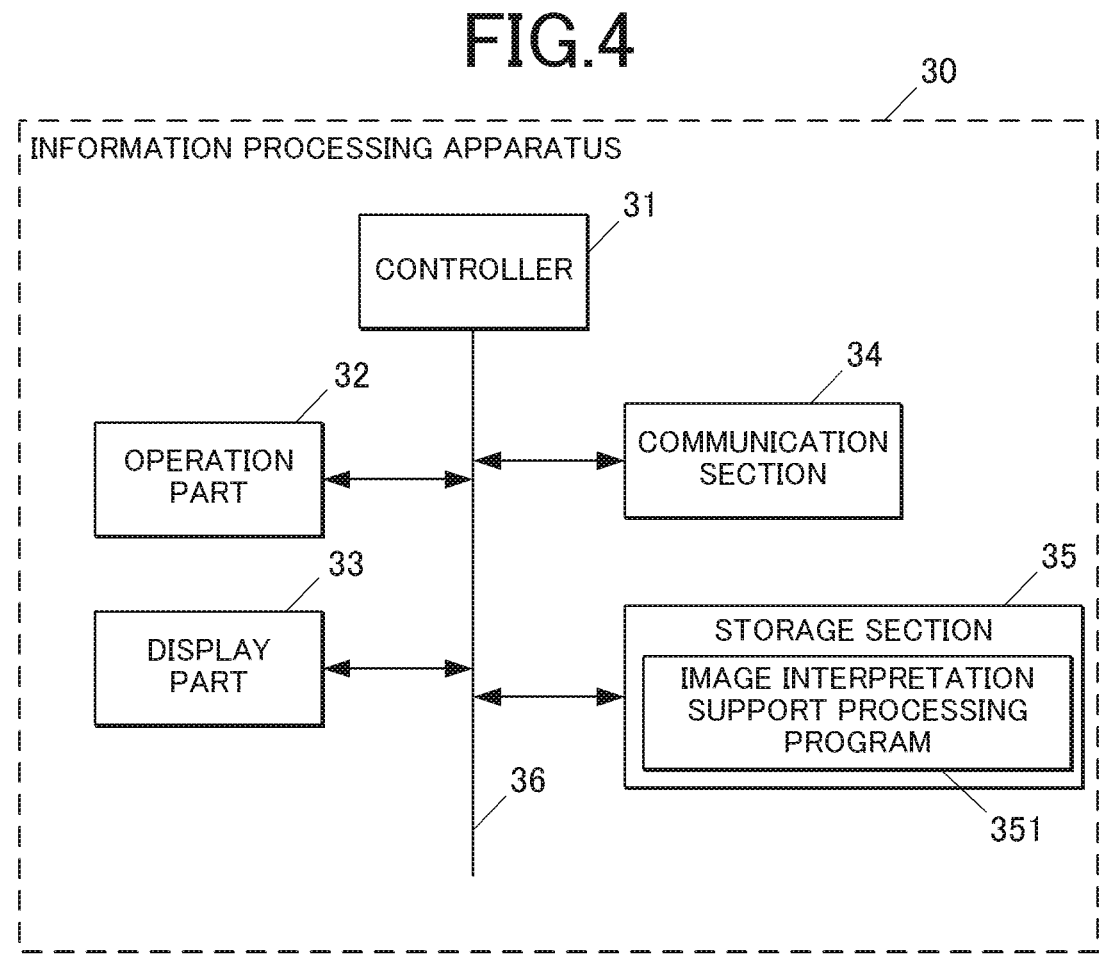
FIG. 4 is a block diagram illustrating a functional configuration of the information processing apparatus.

FIG. 4 shows the functional configuration of the information processing apparatus 30. The information processing apparatus 30 includes a controller 31 (hardware processor), an operation part (or operation device) 32, a display part (or display device) 33, a communication section (or communication interface) 34, a storage section (or storage) 35, and the like. Each unit of the information processing apparatus 30 is connected by a bus 36.

The controller 31 includes a CPU, a RAM, and the like. The controller 31 integrally controls the processing operation of each unit of the information processing apparatus 30. Specifically, the controller 31 reads various processing programs or instructions stored in the storage section 35, loads the programs or instructions to the RAM, and performs various types of processing in accordance with the programs or instructions.

The operation part 32 includes a keyboard having cursor keys, character/number input keys, various function keys, and the like, and a pointing device such as a mouse. The operation part 32 outputs an operation signal input by a key operation on the keyboard or an operation of the mouse to the controller 31. In addition, in a case where the operation part 32 is configured by a touch panel laminated on the display part 33, the operation part 32 outputs an operation signal corresponding to a position of a touch operation by a user's finger or the like to the controller 31.

The display part 33 is configured to include a monitor such as a liquid crystal display (LCD), and displays various screens according to an instruction of a display signal input from the controller 31.

The communication section 34 includes a network interface and the like, and transmits and receives data to and from an external device connected via the communication network N.

The storage section 35 includes an HDD, a nonvolatile semiconductor memory, and the like. The storage section 35 stores various processing programs or instructions, parameters and files necessary for execution of the programs or instructions, and the like. For example, an image interpretation support processing program 351 is stored in the storage section 35. The image interpretation support processing program 351 is a program or instructions for executing image interpretation support processing (see FIG. 6) to be described later.

In the image interpretation support processing, the controller 31 acquires information on whether or not each of the lesion detection regions obtained by the computer processing is false positive, which is input by the user for the first analysis result including at least one lesion detection region obtained by the computer processing for the first medical image of the patient.

Further, the controller 31 acquires a second analysis result including at least one lesion detection region obtained by computer processing on the second medical image of the patient.

In addition, the controller 31 displays a region corresponding to the lesion detection region included in the first analysis result for which the information indicating that the region is false positive is acquired, among the lesion detection regions included in the second analysis result, in a display manner different from that of the region corresponding to the lesion detection region included in the first analysis result for which the information indicating that the region is not false positive is acquired.

The first medical image is an image captured at a date and time different from that of the second medical image. In one or more embodiments, the first medical image is a past image, and the second medical image is a current image. The current image is a newly captured medical image to be interpreted. The past image is a medical image captured in the past with the same patient as the current image as an imaging target. In a case where there are a plurality of medical images whose imaging date and time is earlier than that of the current image, the past image is the most recently imaged medical image. In one or more embodiments, the first analysis result is an analysis result obtained by computer processing on the past image. The second analysis result is an analysis result obtained by the computer processing on the current image.

Further, in one or more embodiments, the "false positive lesion detection region in the past image" refers to a lesion detection region included in the analysis result of the past image for which the user has input information indicating false positive. That is, the "false positive lesion detection region in the past image" refers to the "lesion detection region included in the first analysis result in which the information indicating false positive is acquired".

Furthermore, the term "lesion detection region that is not false positive in a past image" refers to a lesion detection region included in the analysis result of a past image for which the user has input information indicating that it is not false positive. That is, the "lesion detection region that is not false positive in the past image" refers to the "lesion detection region included in the first analysis result in which the information indicating that the lesion is not false positive is acquired".

Further, the controller 31 acquires a lesion input region input by the user for the first analysis result including at least one lesion detection region obtained by computer processing for the first medical image of the patient.

In addition, the controller 31 displays a region which is a region excluding the region corresponding to the lesion detection region included in the first analysis result, from which the information indicating false positive has been acquired, among the lesion detection regions included in the second analysis result and does not correspond to the lesion input region in a display manner different from that of the region corresponding to the lesion input region and the region corresponding to the lesion detection region included in the first analysis result, from which the information indicating false positive has been acquired.

[Operation in Medical Image Display System]

Next, the operation of the medical image display system 100 will be described.

FIG. 5 is a flowchart illustrating medical image analysis processing executed by the medical image management server 10. This processing is realized by software processing in cooperation between the CPU of the controller 11 and the program or instructions stored in the storage section 14.

In the medical image management server 10, when a medical image obtained by imaging a patient is received from the modality 20 via the communication section 12 (step S1), the controller 11 allows the storage section 14 to store the received medical image in the medical image storage area 143 (step S2). Furthermore, the controller 11 stores, in a data management table 142 (see FIG. 3) in the storage section 14, the image ID, the patient ID, the imaging date and time, the modality, the site, the direction, and the like included in the image attribute information on the received medical image in an associated manner.

Next, the controller 11 causes the image analysis section 13 to analyze the received medical image (step S3). The image analysis section 13 analyzes the medical image by artificial intelligence (AI) to acquire a lesion detection region and generates data of an analysis result including information on the acquired lesion detection region.

Next, the controller 11 causes the storage section 14 to store the analysis result obtained by the image analysis section 13 in association with the medical image (step S4) and ends the medical image analysis processing. Specifically, the controller 11 causes the analysis result storage area 144 of the storage section 14 to store the analysis result. Further, the controller 11 stores the analysis result ID of the analysis result in the record corresponding to the medical image set as the analysis target in the data management table 142 of the storage section 14.

When a user (doctor) inputs a user ID and a password by operating the operation part 32 in order to access the medical image management server 10 from the information processing apparatus 30, the controller 31 transmits the input user ID and password to the medical image management server 10 via the communication section 34.

In the medical image management server 10, when the user ID and the password are received by the communication section 12, the controller 11 determines whether or not the received user ID and password match any of the combinations of user IDs and passwords registered in advance in the user management table 141 of the storage section 14. If the controller 11 determines that there is a match, the controller 11 permits the user of the information processing apparatus 30 to use the information processing apparatus 30.

Figure 6:
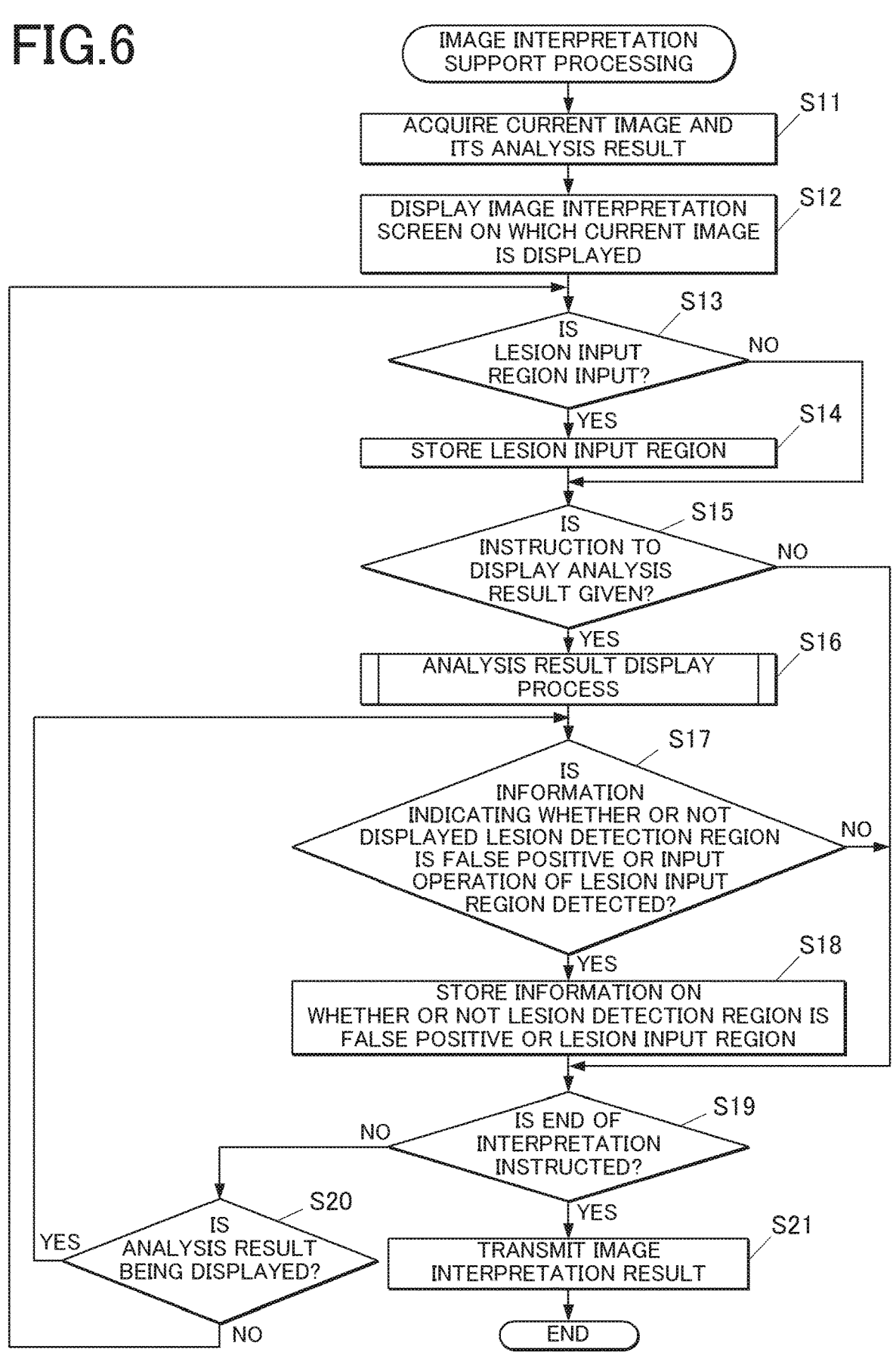
FIG. 6 is a flowchart illustrating image interpretation support processing executed by the information processing apparatus.

FIG. 6 is a flowchart illustrating the image interpretation support processing executed by the information processing apparatus 30. This processing is realized by software processing in cooperation with the CPU of the controller 31 and the image interpretation support processing program 351 stored in the storage section 35.

In the image interpretation support process, the controller 31 acquires the current image (second medical image) and its analysis result (second analysis result) from the medical image management server 10 via the communication section 34 (step S11).

For example, the controller 31 transmits an acquisition request for a medical image including an image ID specified by a user's operation on the operation part 32 to the medical image management server 10 via the communication section 34. The controller 11 of the medical image management server 10 reads, from the medical image storage area 143, the medical image corresponding to the image ID included in the acquisition request, and transmits the medical image to the information processing apparatus 30 via the communication section 12. Further, the controller 11 refers to the data management table 142 of the storage section 14, and specifies the "analysis result ID" from the record corresponding to the "image ID" of the current image. The controller 11 reads an analysis result corresponding to the specified "analysis result ID" from the analysis result storage area 144, and transmits the analysis result to the information processing apparatus 30 via the communication section 12.

Note that the controller 31 may acquire the current image from the modality 20.

Next, the controller 31 displays the image interpretation screen 331 on which the acquired current image is displayed on the display part 33 (step S12).

Figure 7:
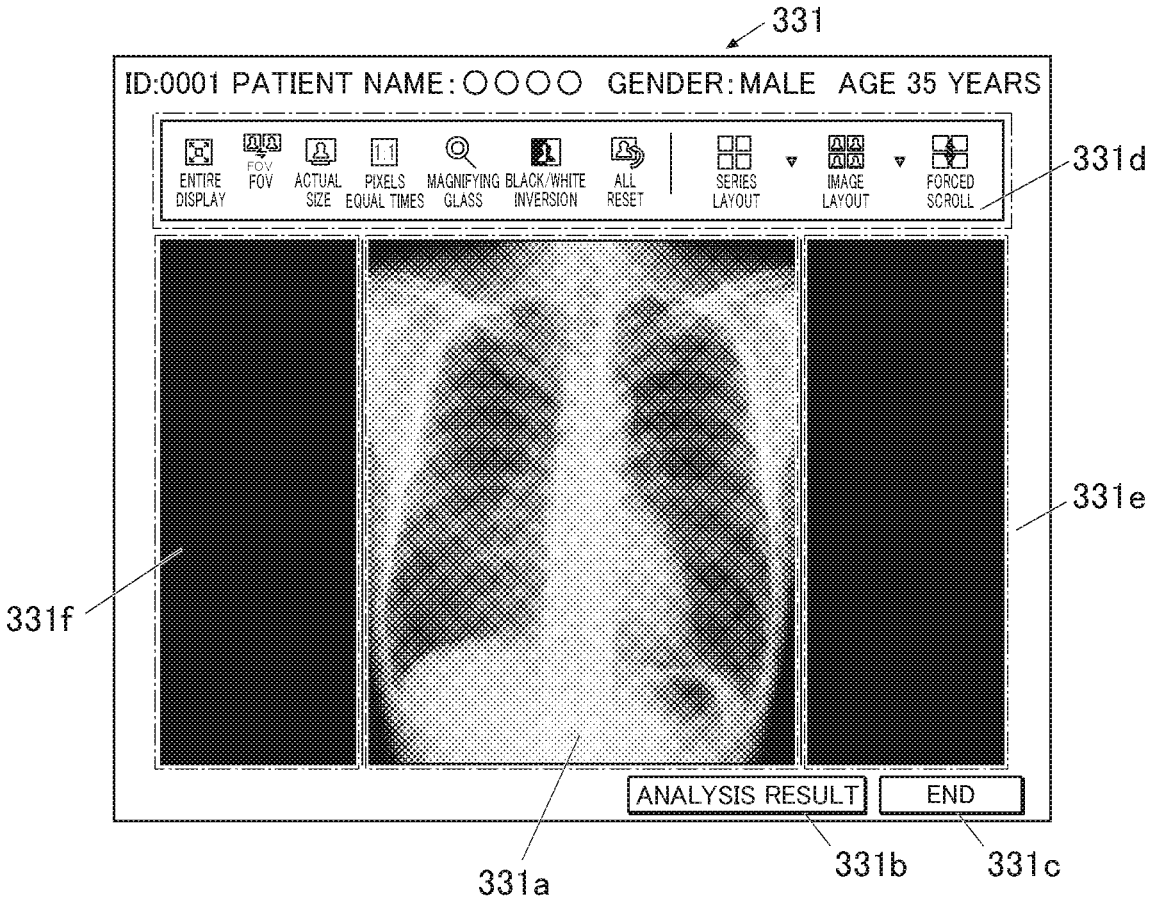
FIG. 7 is a view illustrating an example of an image interpretation screen.

The image interpretation screen is a screen for displaying a medical image and allowing a user (doctor) to perform image interpretation and input an image interpretation result. FIG. 7 illustrates an example of the image interpretation screen 331. As illustrated in FIG. 7, the image interpretation screen 331 includes a medical image display region 331a, an analysis result display button 331b, an end button 331c, a tool display region 331d, and the like. The medical image display region 331a is a region for displaying a medical image to be interpreted. The button 331b for displaying analysis result is a button for instructing to display the analysis result. The end button 331c is a button for giving an instruction to end the interpretation.

For example, when the doctor who is the user designates (for example, right-clicks) the position of a region considered to be a lesion on the medical image displayed on the image interpretation screen 331 using the operation part 32, a menu item ((e.g., a right-click menu) including the type of lesion is displayed near the designated position on the image interpretation screen 331. When the type of lesion in a specified region is selected from among the menu items by an operation of the operation part 32, supplementary information (e.g., annotation information) indicating a lesion detection region (lesion input region) detected by the user is appended to the specified region, and the specified region is input as a lesion input region. Information on the lesion input region (the position of the lesion input region, the type of lesion, the content of the supplementary information, and the like) is primarily stored in the RAM.

In a case where the image interpretation screen 331 is displayed, the controller 31 determines whether or not an input operation of the lesion input region is detected by the operation part 32 (step S13).

In a case where it is determined that the input operation of the lesion input region is not detected (step S13; NO), the controller 31 proceeds to step S15.

When it is determined that the input operation of the lesion input region is detected (step S13; YES), the controller 31 stores the input information of the lesion input region in the RAM (step S14), and proceeds to step S15.

In step S15, the controller 31 determines whether an instruction to display an analysis result has been given (step S15).

The analysis result is a detection result of the lesion detection region by the computer processing. For example, in a case where the analysis result display button 331b is pressed by the operation part 32, the controller 31 determines that the display of the analysis result is instructed.

When it is determined that the display of the analysis result is not instructed (Step S15; NO), the controller 31 proceeds to Step S19.

When it is determined that the display of the analysis result is instructed (step S15; YES), the controller 31 executes an analysis result display process (step S16).

FIG. 8 is a flowchart illustrating analysis result display process executed by the information processing apparatus 30. This processing is realized by software processing in cooperation between the CPU of the controller 31 and the analysis result display process program or instructions stored in the storage section 35.

First, the controller 31 inquires of the medical image management server 10 via the communication section 34 whether a past image (first medical image) of the same patient as the current image exists (step S161).

For example, the controller 31 transmits the image ID of the current image to the medical image management server 10 to inquire whether there is a past image of the same patient as the current image. The controller 11 of the medical image management server 10 refers to the data management table 142 in the storage section 14 and determines whether or not a medical image whose "patient ID", "modality", "site", and "direction" are common to those of the current image exists in the medical image storage area 143. Then, the controller 11 notifies the information processing apparatus 30 of the determination result via the communication section 12.

When it is notified from the medical image management server 10 that there is no past image of the same patient as the current image (step S161; NO), the controller 31 displays supplementary information (annotation information) in the lesion detection region included in the analysis result acquired in step S11 of the displayed current image (step S162), and proceeds to step S17 in FIG. 6.

When being notified by the medical image management server 10 that a past image of the same patient as the current image exists (step S161; YES), the controller 31 acquires the past image (first medical image) and its interpretation result from the medical image management server 10 via the communication section 34 (step S163).

The controller 11 of the medical image management server 10 refers to the data management table 142 of the storage section 14, and extracts a record which is a medical image having the "patient ID", the "modality", the "site", and the "direction" in common with the current image and has the "imaging date and time" before the current image and the latest. Next, the controller 11 acquires an image ID (image ID of a past image) included in the extracted record. Then, the controller 11 reads out the medical image corresponding to the acquired image ID from the medical image storage area 143 of the storage section 14. Further, the controller 11 refers to the data management table 142, and specifies the "image interpretation result ID" from the record corresponding to the acquired image ID. Next, the controller 11 reads an image interpretation result corresponding to the "image interpretation result ID" from the image interpretation result storage area 145. Then, the controller 11 transmits the read medical image (past image) and interpretation result to the information processing apparatus 30 via the communication section 12.

Next, the controller 31 compares the analysis result of the current image with the interpretation result of the past image, and determines whether or not there is a region corresponding to false positive lesion detection region in the past image in the lesion detection region included in the analysis result of the current image (lesion detection region of the current image) (step S164).

In step S164, the controller 31 executes, for example, the following processes (1) to (4) to determine whether or not there is a region corresponding to false positive lesion detection region in the past image in the lesion detection region included in the analysis result of the current image.

(1) First, the controller 31 aligns the current image and the past image. Specifically, the controller 31 performs enlargement, reduction, rotation processing, or the like on both or one of the current image and the past image, and aligns the positions of bones, organs, and the like in the images between the current image and the past image.

(2) Next, the controller 31 adjusts the positions of the lesion detection region included in the analysis result of the current image and the false positive lesion detection region in the past image in accordance with the alignment between the current image and the past image. Specifically, the controller 31 converts the position of the lesion detection region included in the analysis result of the current image or the position of the false positive lesion detection region in the past image into a position after the alignment of each image.

(3) Next, the controller 31 superimposes the lesion detection region included in the analysis result of the current image after the position adjustment and the false positive lesion detection region in the past image and calculates the degree of overlap between each lesion detection region included in the analysis result of the current image and each lesion detection region included in the analysis result of the past image.

For example, in a case where the position of the lesion detection region is designated by one point (center position), the controller 31 calculates a ratio (degree of overlap) at which regions in a range designated in advance ((e.g., within a predetermined radius) from the lesion center position in the lesion detection region of the current image and the false positive lesion detection region in the past image overlap each other. Here, the range designated in advance can be changed for each medical facility, requesting department, modality, or imaging site. The medical facility is a medical facility in which the imaging is performed or a medical facility to which the user belongs. Furthermore, the user (doctor) may specify any value as the previously specified range.

For example, in a case where the position of the lesion detection region is designated by a region, the controller 31 calculates a ratio (degree of overlap) at which the lesion detection region of the current image and the lesion detection region of the false positive in the past image overlap.

(4) Next, the controller 31 determines whether or not the degree of overlap between each lesion detection region included in the analysis result of the current image and each false positive lesion detection region included in the analysis result of the past image is equal to or more than a predetermined threshold value. The threshold value used here may be changed for each medical facility, request department, imaging site, or user.

In a case in which the degree of overlap between the lesion detection region of the current image and the false positive lesion detection region of the past image is equal to or greater than a predetermined threshold value, the controller 31 determines that the lesion detection region of the current image for which the degree of overlap has been calculated matches the false positive lesion detection region of the past image. That is, the controller 31 determines that the lesion detection region of the current image for which the degree of overlap is calculated is a region corresponding to false positive lesion detection region in the past image. In a case in which the degree of overlap between the lesion detection region of the current image and the false positive lesion detection region of the past image is less than the predetermined threshold value, the controller 31 determines that the lesion detection region of the current image for which the degree of overlap has been calculated and the false positive lesion detection region of the past image do not match each other. That is, the controller 31 determines that the lesion detection region of the current image for which the degree of overlap is calculated is not a region corresponding to false positive lesion detection region in the past image. When there is at least one region corresponding to the false positive lesion detection region in the past image among the lesion detection regions of the current image, the controller 31 determines that there is a region corresponding to the false positive lesion detection region in the past image among the lesion detection regions included in the analysis result of the current image.

Without calculating the degree of overlap in (3) to (4) described above, a region that coincides with, partially overlaps with, or includes false positive lesion detection region in the past image among the lesion detection regions in the current image may be simply determined as a region corresponding to the false positive lesion detection region in the past image.

In a case in which it is determined in Step S164 that there is a region corresponding to false positive lesion detection region in the past image among the lesion detection regions included in the analysis result of the current image (Step S164; YES), the controller 31 displays a region corresponding to a false positive lesion detection region in the past image among the lesion detection regions of the current image in a display manner different from that of a region corresponding to a non-false positive lesion detection region in the past image (Step S165).

Figure 9:
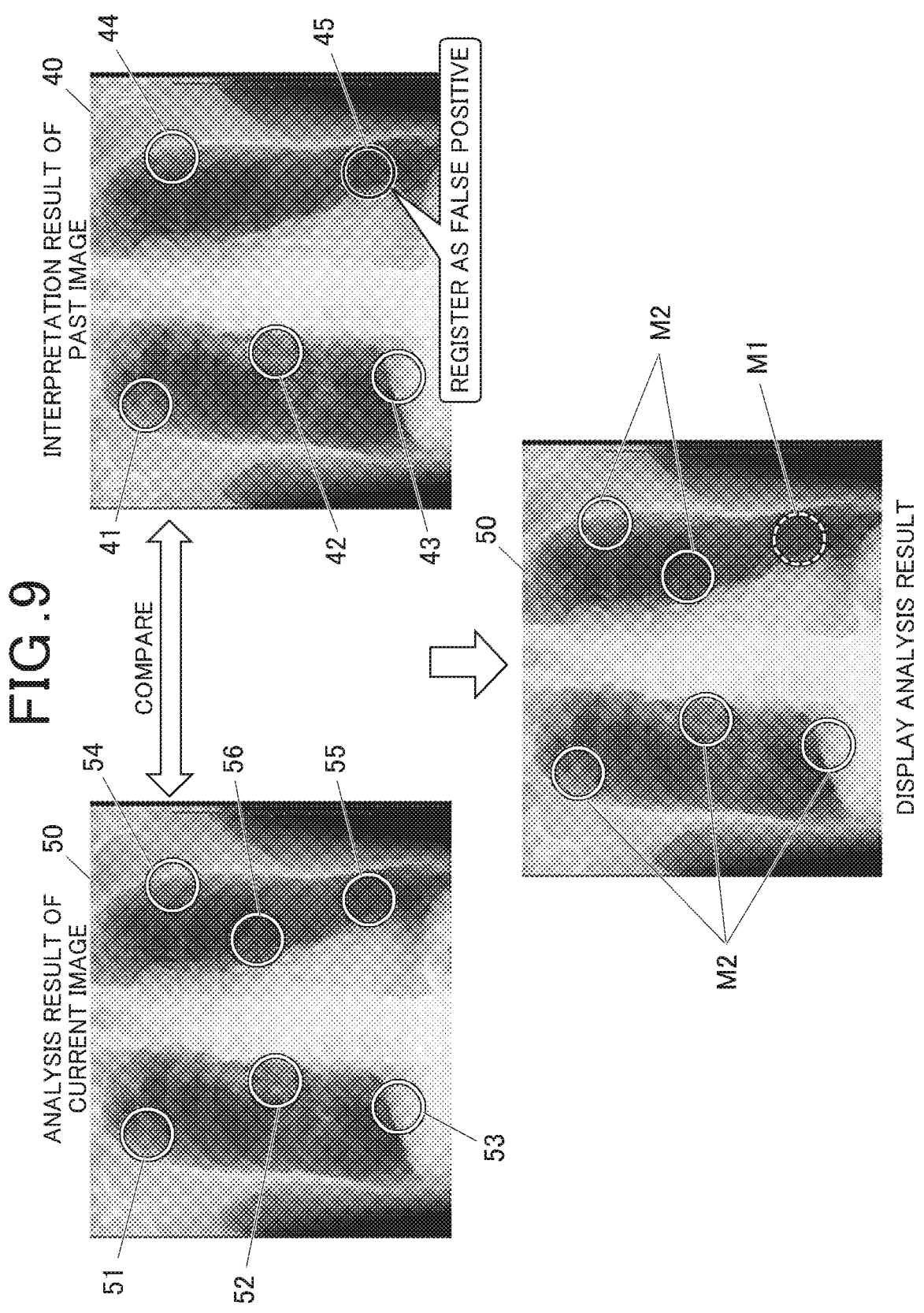
FIG. 9 is a diagram showing a display example of the analysis result of the current image in one or more embodiments.

For example, in the current image 50 illustrated in FIG. 9, when regions corresponding to the lesion detection regions 41 to 45 in the past image 40 are lesion detection regions 51 to 55, respectively, and the lesion detection region 45 is false positive lesion detection region, the controller 31 causes the lesion detection region 55, which is a region corresponding to the lesion detection region 45, to be displayed in a different manner from the lesion detection regions 51 to 54 in the current image 50 displayed on the image interpretation screen 331. For example, as illustrated in "analysis result display" of FIG. 9, the controller 31 displays first supplementary information (annotation information) M1 to be attached to the lesion detection region 55 in a display manner different from a display manner of second supplementary information (annotation information) M2 to be attached to the other lesion detection regions 51 to 54. For example, the controller 31 displays the first supplementary information M1 so as to be highlighted with respect to the second supplementary information M2 by making at least one selected from the group of a shape, a line type, a thickness, a color, a brightness, a transparency, or a symbol of the first supplementary information M1 different from that of the second supplementary information M2. Alternatively, the controller 31 may add at least one piece of identification information of a character or a symbol to the first supplementary information M1 to highlight the first supplementary information M1 with respect to the second supplementary information M2. FIG. 9 shows an example in which the first supplementary information M1 is highlighted with respect to the second supplementary information M2 by changing the line type of the first supplementary information M1.

Figure 10:
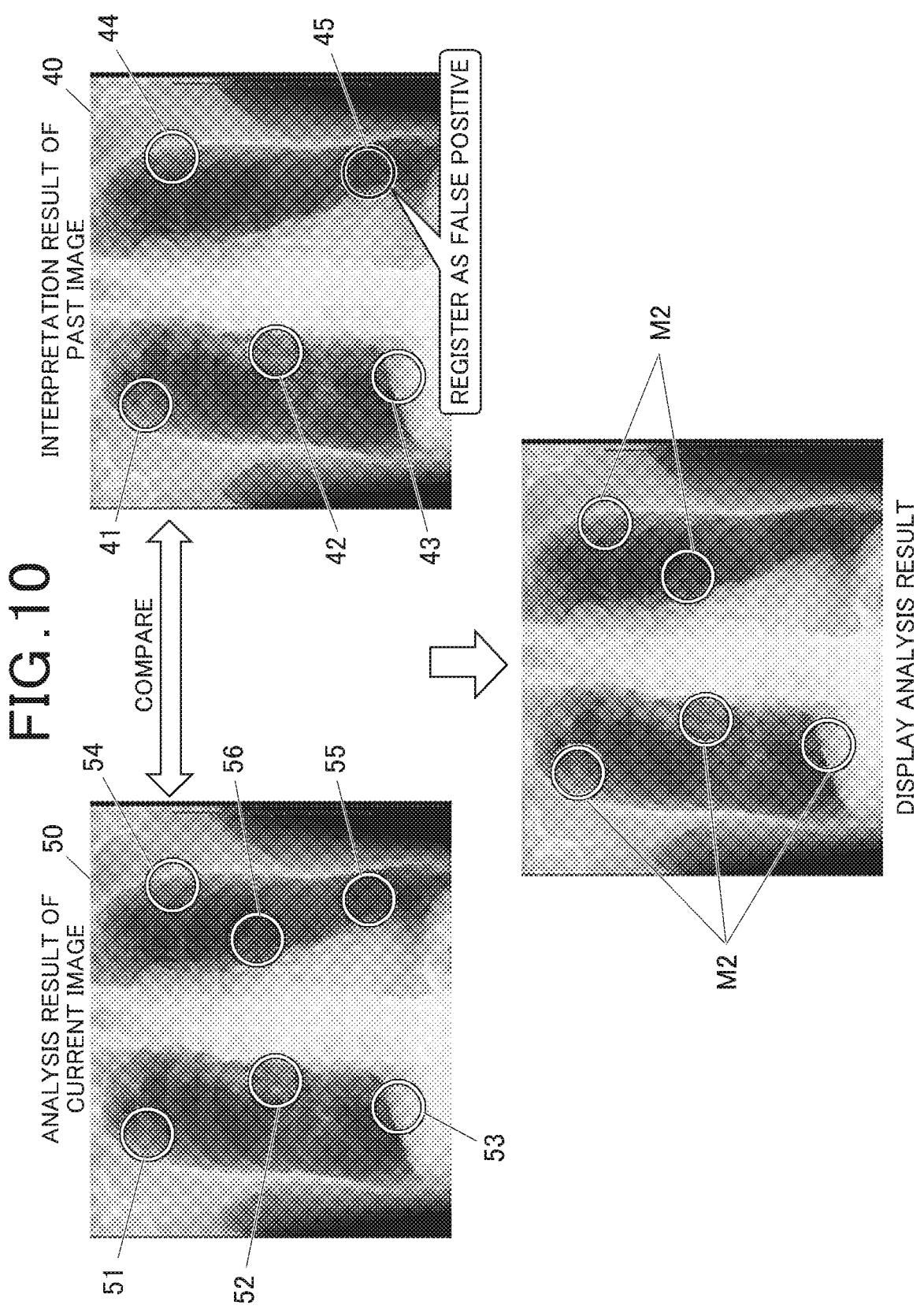
FIG. 10 is a diagram showing a display example of the analysis result of the current image in one or more embodiments.

Alternatively, as illustrated in FIG. 10, the controller 31 may cause the lesion detection region 55 to be displayed in a manner different from that of the lesion detection regions 51 to 54 by refraining from displaying the first supplementary information in the lesion detection region 55.

In addition, the controller 31 warns the user that there is a region corresponding to the false positive lesion detection region in the past image in the lesion detection region included in the analysis result of the current image (step S166), and proceeds to step S167.

In step S166, the controller 31 warns the user by, for example, notifying the user of predetermined information, changing and displaying the display manner of the mouse cursor of the image interpretation screen 331, or changing and displaying the display manner of the window of the image interpretation screen 331. The change of the display manner of the window includes, for example, changing a color of a region serving as a background in the window with respect to the medical image display region 331a in the window. The area serving as the background includes, for example, a tool display region 331d in a window.

For example, as illustrated in FIG. 11, the controller 31 displays, on the image interpretation screen 331, a pop-up window 332 for notifying that the lesion detection region determined to be false positive in the past image is detected from the current image.

Figure 12:
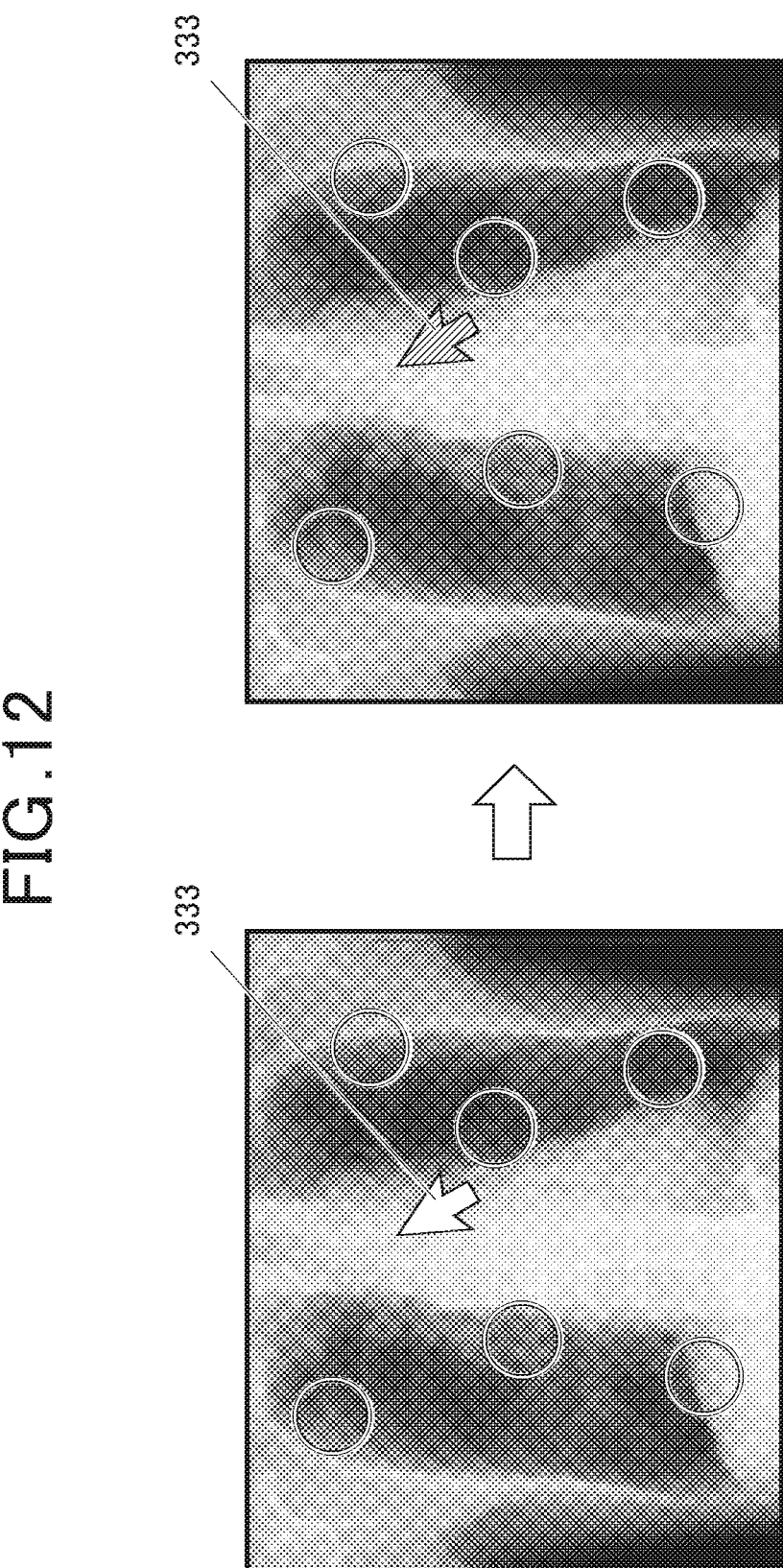
FIG. 12 is a diagram showing a display example (change of display manner of the mouse cursor) for notifying the user that a region corresponding to a region registered as false positive in the past image is included in the lesion detection region of the analysis result of the current image.

Alternatively, as illustrated in FIG. 12, the controller 31 changes the color of the mouse cursor 333 for display. The controller 31 may change the shape of the mouse cursor 333 for display.

Figure 13:
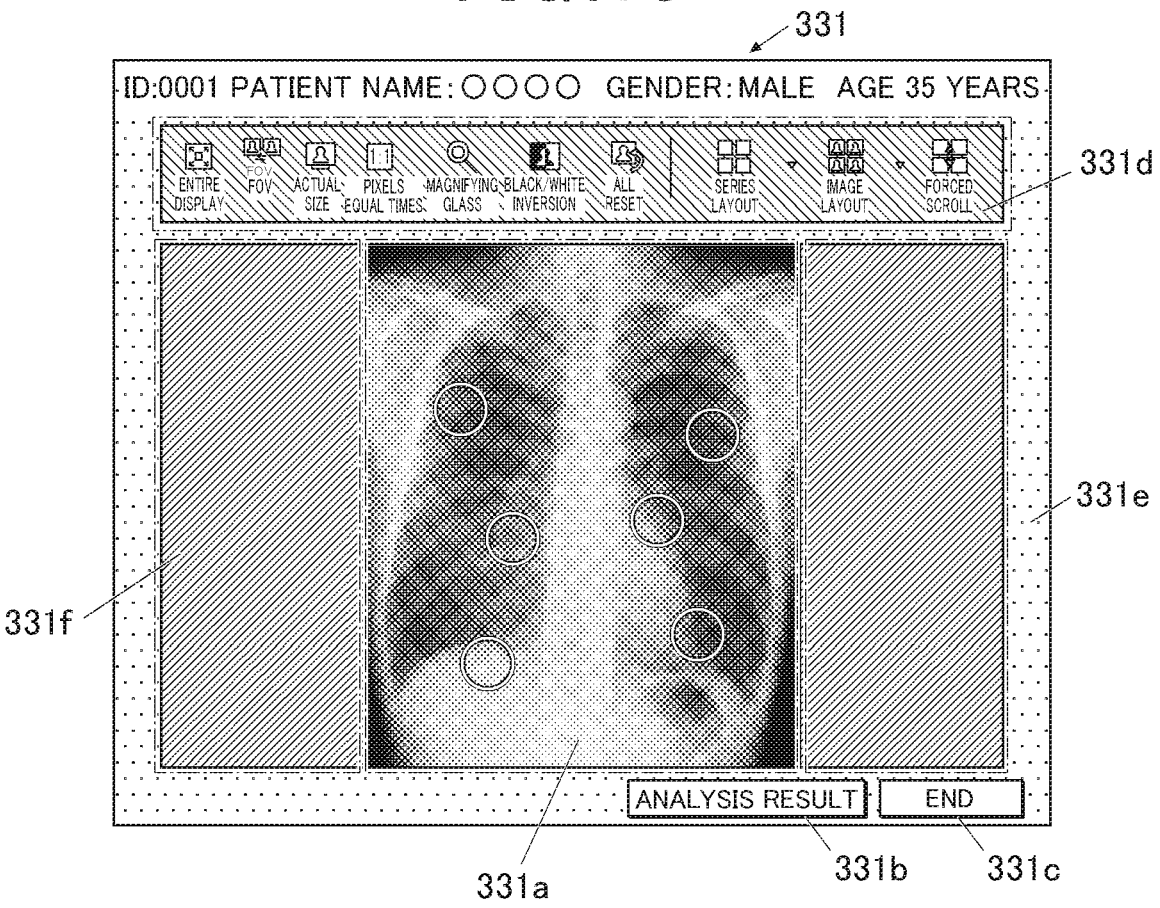
FIG. 13 is a diagram showing a display example (change of display manner of a window) for notifying the user that a region corresponding to a region registered as false positive in the past image is included in the lesion detection region of the analysis result of the current image.

Alternatively, as shown in FIG. 13, the controller 31 changes the color of the window frame 331e of the image interpretation screen 331 from the color of the normal display (see FIG. 7) and displays it. Alternatively, the controller 31 causes the medical image display region 331a in the window to be displayed with at least one of the regions 331d and 331f serving as the background in the window being changed in color.

On the other hand, in Step S164, in a case where it is determined that there is no region corresponding to the false positive lesion detection region in the past image in the lesion detection region included in the analysis result of the current image (Step S164; NO), the controller 31 proceeds to Step S167.

In Step S167, the controller 31 compares a region excluding a region corresponding to false positive lesion detection region in the past image among the lesion detection regions included in the analysis result of the current image with a lesion input region input by the user in the past image included in the interpretation result of the past image. Then, the controller 31 determines whether there is a region that does not correspond to the lesion input region of the past image in a region excluding a region corresponding to false positive lesion detection region in the past image, in the lesion detection region of the current image (step S167).

In a case where it is determined that there is a region that does not correspond to the lesion input region input by the user in the past image in the region excluding the region corresponding to the false positive lesion detection region in the past image among the lesion detection regions of the current image (step S167; YES), the controller 31 displays the lesion detection region of the current image that is a region excluding the region corresponding to the false positive lesion detection region in the past image and is determined not to correspond to the lesion input region in the past image in a display manner different from the region corresponding to the lesion detection region determined to correspond to the lesion input region in the past image and the region corresponding to the false positive lesion detection region in the past image among the lesion detection regions of the current image (step S168). Next, the controller 31 proceeds to step S17 in FIG. 6.

For example, in a case where the lesion detection region 56 in FIG. 9 is a lesion detection region determined not to correspond to the lesion input region input by the user in the past image, the controller 31 displays the lesion detection region 56 in a different manner from the lesion detection regions 51 to 55.

Figure 14:
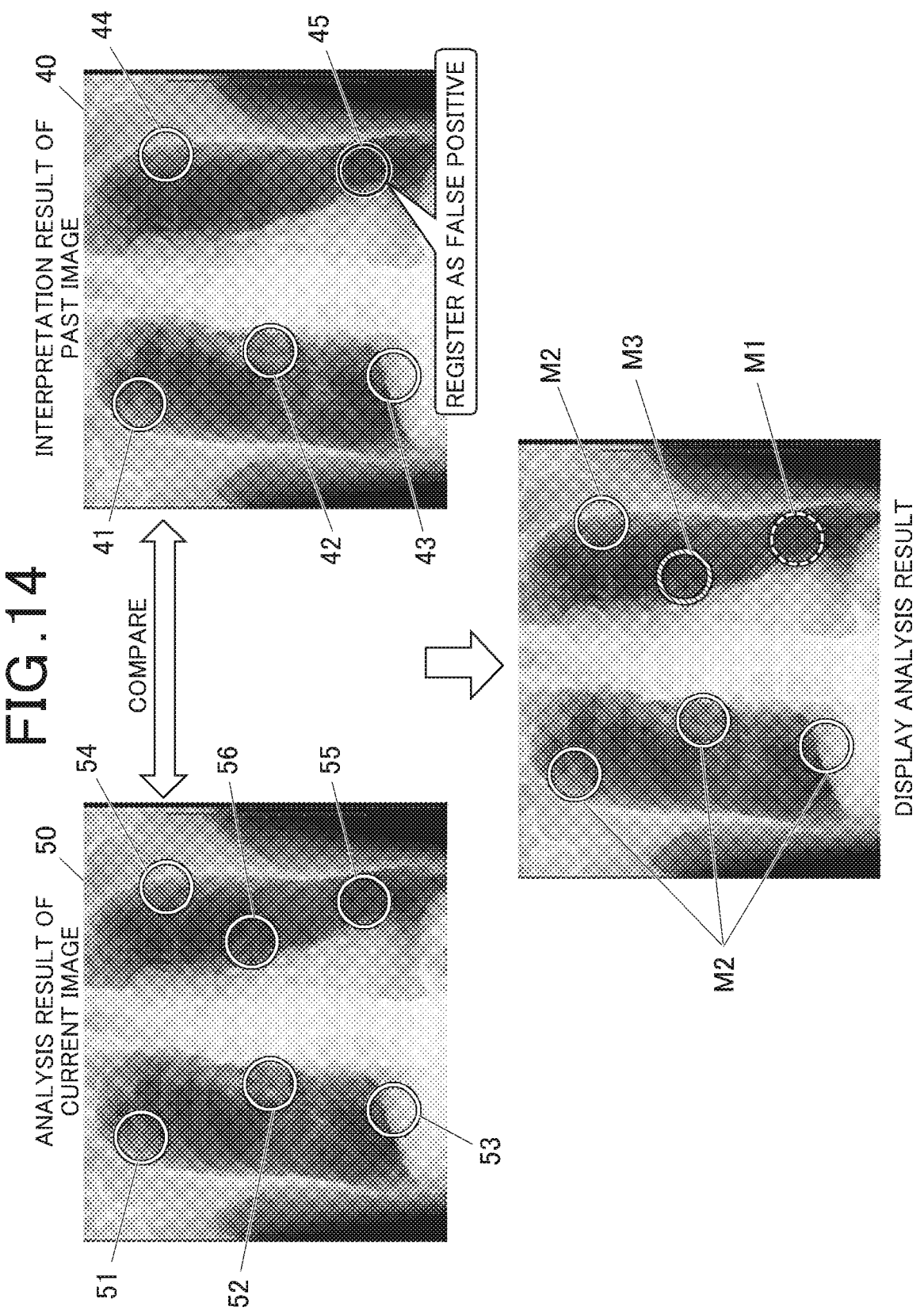
FIG. 14 is a diagram illustrating a display example of the analysis result of the current image in one or more embodiments.
Figure 15:
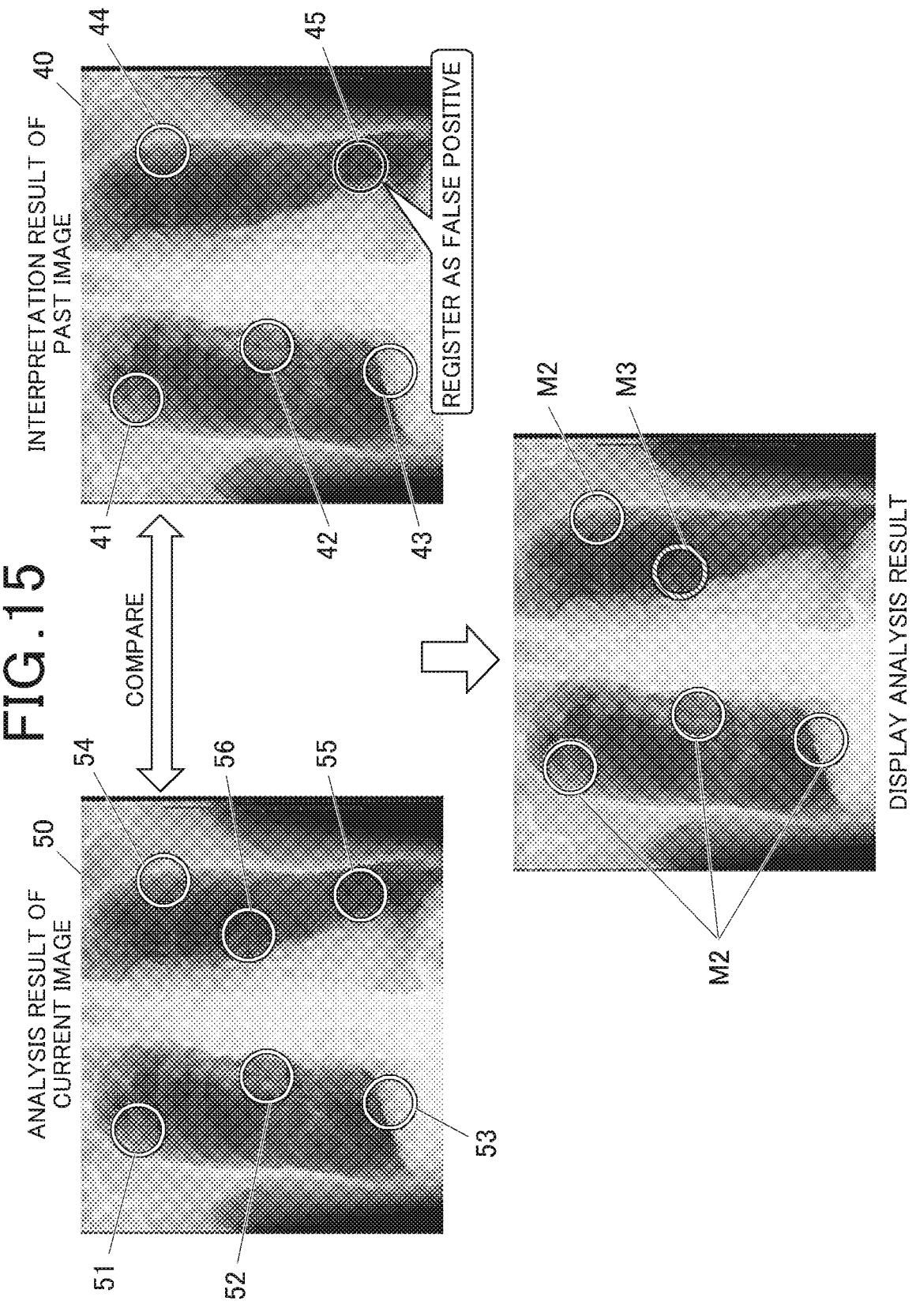
FIG. 15 is a diagram illustrating an example of displaying an analysis result of the current image in one or more embodiments.

For example, as illustrated in FIG. 14, the controller 31 displays the third supplementary information (annotation information) M3 to be attached to the lesion detection region 56 in a different display manner from the first supplementary information M1 and the second supplementary information M2 to be attached to the other lesion detection regions 51 to 55. In FIG. 14, the controller 31 displays and highlights the third supplementary information M3 differently from the first supplementary information M1 and the second supplementary information M2 by changing the line type from the first supplementary information M1 and changing the color (brightness) from the second supplementary information M2. In a case in which the first supplementary information M1 is not displayed, as illustrated in FIG. 15, the controller 31 displays the third supplementary information M3 to be attached to the lesion detection region 56 in a display manner different from that of the second supplementary information M2 to be attached to the other lesion detection regions 51 to 54.

As a result, among the lesion detection regions obtained by the computer processing from the current captured image (current image), a region excluding a region corresponding to the false positive lesion detection region in the past image and not corresponding to the lesion input region input by the user in the past image is displayed in a different manner from the region corresponding to the lesion input region in the past image and the region corresponding to the false positive lesion detection region. In this way, one or more embodiments provide a practical improvement for allowing the user to easily grasp a new lesion detection region obtained by computer processing from the captured image of this time (current image).

Note that according to one or more embodiments, the lesion input region that the user has input in the past image is a region that the user has directly specified as a lesion candidate in the past image, but there is no limitation thereto. For example, the lesion input region input by the user in the past image may be set as a region determined not to be false positive in the information on whether or not to be false positive input by the user for each lesion detection region of the analysis result of the past image. Alternatively, a lesion input region input by the user in the past image may be set as a region obtained by combining a region directly designated as a lesion candidate by the user in the past image and a region determined not to be false positive in the information on whether a lesion is false positive input by the user for each lesion detection region of the analysis result of the past image.

On the other hand, in a case where it is determined in Step S167 that a region not corresponding to the lesion input region input by the user in the past image is not present in the lesion detection region of the current image (Step S167; NO), the controller 31 proceeds to Step S17 of FIG. 6.

Here, in a case where the analysis result is displayed, the user can input information on whether or not the displayed lesion detection region is false positive on the image interpretation screen 331.

For example, when the supplementary information (annotation information) displayed on the medical image (current image) displayed on the image interpretation screen 331 is selected ((e.g., right-clicked) by the operation part 32, the controller 31 displays the items of "register as false positive" and "register as true positive" in the menu item (for example, right-clicked menu). The doctor who is the user selects "register as false positive" or "register as true positive" from the displayed menu items using the operation part 32, and thus can input information regarding whether or not the lesion detection region indicated by the selected supplementary information is false positive. In order to simplify the input operation, only "register as false positive" may be displayed in the menu item, only the lesion detection region determined as false positive by the doctor may be input, and a region without input may be considered to be input as true positive. Alternatively, only "register as true positive" may be displayed in the menu item, only the lesion detection region determined as true positive by the doctor may be input, and a region without an input may be considered to be input as false positive. Note that it is also possible for the user to subsequently input a lesion input region.

In step S17 of FIG. 6, the controller 31 determines whether or not information indicating whether or not the displayed lesion detection region is false positive or an input operation in the lesion input region has been detected (step S17).

In a case where it is determined that the information regarding whether or not the displayed lesion detection region is false positive or the input operation of the lesion input region is not detected (step S17; NO), the controller 31 proceeds to step S19.

In a case where it is determined that the information on whether or not the displayed lesion detection region is false positive or the input operation of the lesion input region is detected (step S17; YES), the controller 31 stores the input information on whether or not the lesion detection region is false positive or the input lesion input region in the RAM (step S18), and the process proceeds to step S19.

In Step S19, the controller 31 determines whether or not the end of the interpretation is instructed by the operation part 32 (Step S19).

For example, in a case where the end button 331c displayed on the image interpretation screen 331 is pressed by the operation part 32, the controller 31 determines that the end of the interpretation is instructed.

In a case where it is determined that the end of the interpretation is not instructed by the operation part 32 (step S19; NO), the controller 31 determines whether or not the analysis result is being displayed (step S20).

When it is determined that the analysis result is being displayed (step S20; YES), the controller 31 returns to step S17.

When it is determined that the analysis result is not being displayed (Step S20; NO), the controller 31 returns to Step S13.

On the other hand, when determining in step S19 that ending of the image interpretation has been instructed by the operation part 32 (step S19; YES), the controller 31 adds the image ID of the current image to the image interpretation result stored in the RAM, transmits the image interpretation result to the medical image management server 10 via the communication section 34 (step S21), and ends the image interpretation support processing. The interpretation result stored in the RAM is information on whether or not the lesion detection region included in the analysis result of the current image is false positive and information on the lesion input region input by the user.

In the medical image management server 10, when the communication section 12 receives the interpretation result from the information processing apparatus 30, the controller 11 stores the received interpretation result in the image interpretation result storage area 145 in association with the medical image. For example, the image interpretation result ID is assigned to the received interpretation result and stored in the image interpretation result storage area 145, a record of the image ID corresponding to the interpretation result is extracted from the data management table 142, and the image interpretation result ID assigned to the received interpretation result is registered in the item of "image interpretation result ID" of the extracted record.

As described above, according to one or more embodiments, the controller 31 of the information processing apparatus 30 acquires information on whether or not each of the lesion detection regions input by the user is false positive with respect to the analysis result (first analysis result) including at least one lesion detection region obtained by the computer processing on the past image (first medical image) of the patient. Further, the controller 31 acquires an analysis result (second analysis result) including at least one lesion detection region obtained by computer processing on the current image (second medical image) of the patient. Then, the controller 31 displays the region corresponding to the false positive lesion detection region in the past image among the lesion detection regions included in the analysis result of the current image in a display manner different from the region corresponding to the non-false positive lesion detection region.

In this way, one or more embodiments provide a practical improvement for allowing the user to recognize false positive region among the lesion detection regions obtained by the computer processing. As a result, it is possible to prevent false positive from being overlooked.

For example, the controller 31 displays first supplementary information (annotation information) to be attached to a region corresponding to false positive lesion detection region in the past image and second supplementary information (annotation information) to be attached to a region corresponding to a lesion detection region that is not false positive among the lesion detection regions included in the analysis result of the current image in different display manners. In this way, one or more embodiments provide a practical improvement for allowing the user to distinguish and recognize false positive lesion detection region and a non-false positive lesion detection region among the lesion detection regions obtained by the computer processing.

Further, for example, the controller 31 does not display the first supplementary information to be attached to a region corresponding to false positive lesion detection region in the past image among the lesion detection regions included in the analysis result of the current image such that a region corresponding to false positive lesion detection region included in the analysis result of the past image is displayed in a display manner different from that of a region corresponding to a non-false positive lesion detection region. In this way, one or more embodiments provide a practical improvement for eliminating the troublesomeness that false positive result is displayed again.

In addition, the controller 31 displays a region which is a region excluding the region corresponding to the false positive lesion detection region in the past image and does not correspond to the lesion input region input by the user among the lesion detection regions included in the analysis result of the current image in a display manner different from the region corresponding to the lesion input region and the region corresponding to the false positive lesion detection region. In this way, one or more embodiments provide a practical improvement for allowing the user to easily recognize, for example, a newly detected region among the lesion detection regions included in the analysis result of the current image.

In addition, when there is a region corresponding to false positive lesion detection region in the past image among the lesion detection regions included in the analysis result of the current image, the controller 31 notifies the user of predetermined information, changes the display manner of the mouse cursor to display, or changes the display manner of the window to display. In this way, one or more embodiments provide a practical improvement for allowing the user to easily recognize that there is a region corresponding to false positive lesion detection region in the past image among the lesion detection regions included in the analysis result of the current image.

In addition, the controller 31 highlights the first supplementary information to be attached to the region corresponding to the false positive lesion detection region in the past image among the lesion detection regions included in the analysis result of the current image, thereby displaying in a display manner different from the region corresponding to the non-false positive lesion detection region in the past image. In this way, one or more embodiments provide a practical improvement for allowing the user to easily recognize the region corresponding to the lesion detection region which is false positive in the past image among the lesion detection regions included in the analysis result of the current image.

Note that the descriptions in the above embodiments are examples of the recording medium storing instructions, the information processing apparatus, the information processing method, and the information processing system, and the present invention is not limited thereto. The detailed configuration and detailed operation of each apparatus constituting the system can also be appropriately changed without departing from the scope of the present invention.

For example, in the above-described embodiments, when the display of the analysis result is instructed, the controller 31 displays the region corresponding to the false positive lesion detection region in the past image among the lesion detection regions obtained by the computer processing in a display manner different from that of the region corresponding to the non-false positive lesion detection region in the past image. Instead, for example, a predetermined operation button such as a switching button may be provided on the image interpretation screen 331, and in a case where the display of the analysis result is instructed, first, the controller 31 may display a region corresponding to false positive lesion detection region in the past image in the same display manner as a region corresponding to a non-false positive lesion detection region in the past image among the lesion detection regions obtained by the computer processing in cooperation with the image interpretation support processing program 351, and may switch the display manner of a region corresponding to false positive lesion detection region in the past image in the lesion detection regions obtained by the computer processing from the same display manner as a region corresponding to a non-false positive lesion detection region in the past image to a different display manner in response to the pressing of the switching button by the user through the operation part 32. For example, the controller 31 may display the first supplementary information to be attached to a region corresponding to false positive lesion detection region in the past image by switching from the same display manner as the second supplementary information to be attached to a region corresponding to a non-false positive lesion detection region in the past image to a different display manner. Alternatively, the controller 31 may display in a display manner different from the first supplementary information by switching the first supplementary information to non-display.

Accordingly, in a case where the user wants to distinguish the region corresponding to the false positive lesion detection region in the past image from the region corresponding to the non-false positive lesion detection region in the past image among the lesion detection regions obtained by the computer processing, the regions can be displayed so as to be distinguished from each other.

Further, each time the above-described switching button is pressed, the first supplementary information to be attached to the region corresponding to the false positive lesion detection region in the past image may be displayed while being switched between (A) display in the same display manner as the second supplementary information to be attached to the region corresponding to the lesion detection region that is not false positive in the past image and (B) display in a different display manner from the second supplementary information to be attached to the region corresponding to the lesion detection region that is not false positive in the past image and (C) non-display.

In the above-described embodiments, the controller 31 displays the first supplementary information to be attached to the region corresponding to the false positive lesion detection region in the past image in a display manner different from that of the second supplementary information to be attached to the region corresponding to the non-false positive lesion detection region in the past image, or does not display the first supplementary information so that the first supplementary information and the second supplementary information are displayed in different display manners. Instead, for example, the controller 31 may hide the second supplementary information in cooperation with the image interpretation support processing program 351 such that both are displayed in different display manners.

In addition, in the above-described embodiments, in a case where the degree of overlap between the lesion detection region of the current image and the false positive lesion detection region in the past image is equal to or greater than the predetermined threshold value, the controller 31 determines that the lesion detection region of the current image and the false positive lesion detection region in the past image, for which the degree of overlap has been calculated, match. That is, the controller 31 determines that the lesion detection region in the analysis result of the current image is a region corresponding to false positive lesion detection region in the past image. However, even in a case where it is determined that there is a match, there may be a suspicion of a mismatch in a case where the degree of overlap is lower than a predetermined reference. Therefore, the controller 31 may display the supplementary information (annotation information) in the region determined as the region corresponding to the false positive lesion detection region in the past image by changing the display depending on whether the degree of overlap is higher or lower than the reference.

The functions executed by the controller 31 of the information processing apparatus 30 in the above embodiments may be provided in an apparatus other than the information processing apparatus 30.

In the above embodiments, the medical image management server 10 has a function of performing computer processing on a medical image and generating an analysis result. However, a device other than the medical image management server 10 may have the analysis function.

In the above-described embodiments, although an example in which a chest image is used as the medical image is illustrated, the imaging site is not limited to the chest. Furthermore, the medical image to be processed may be a plurality of slice images obtained by CT or the like, a multi-frame image (moving image), or an image obtained by three-dimension conversion of an image obtained by CT, MRI, or the like.

Further, for example, the analysis result may be automatically hidden in a case where the display of the supplementary information (annotation information) is obstructive, for example, when a moving image of a multi-frame image is reproduced or when measurement is performed.

In the above-described embodiments, the image data of the medical image, the data of the analysis result, and the data of the interpretation result are stored in different areas in the medical image management server 10. However, at least one of the data of the analysis result and the data of the interpretation result may be incorporated into the medical image file including the image data of the medical image.

In addition, the program or instructions for executing each process in each device described above may be stored in a portable recording medium. Furthermore, a carrier wave may be applied as a medium for providing data of the program or instructions via a communication line.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A non-transitory computer-readable recording medium storing instructions causing a computer to execute:

acquiring information on whether a first lesion detection region input by a user with respect to a first analysis result is false positive, wherein the first analysis result includes one or more first lesion detection regions obtained by computer processing on a first medical image of a patient;

acquiring a second analysis result including one or more second lesion detection regions that are obtained by computer processing on a second medical image of the patient; and among the one or more second lesion detection regions, displaying a false correspondence region in a different manner from a manner of displaying a non-false correspondence region, wherein the false correspondence region corresponds to, among the one or more first lesion detection regions, a first lesion detection region indicated as being false positive in the acquired information, and the non-false correspondence region corresponds to, among the one or more first lesion detection regions, a first lesion detection region indicated as being not false positive in the acquired information.

2. The recording medium according to claim 1, wherein the displaying includes displaying first supplementary information attached to the false correspondence region and second supplementary information attached to the non-false correspondence region in different manners from each other.

3. The recording medium according to claim 2, wherein the displaying includes displaying the false correspondence region in a manner different from a manner of displaying the non-false correspondence region by hiding the first supplementary information attached to the false correspondence region.

4. The recording medium according to claim 2, wherein the first supplementary information and the second supplementary information are annotation information.

5. The recording medium according to claim 2, wherein the displaying includes displaying the false correspondence region in a manner different from a manner of displaying the non-false correspondence region by displaying the first supplementary information attached to the false correspondence region and by refraining from displaying the second supplementary information attached to the non-false correspondence region.

6. The recording medium according to claim 1, wherein the displaying includes displaying the false correspondence region by switching from a same manner as a manner of displaying the non-false correspondence region to a different manner by a predetermined user operation.

7. The recording medium according to claim 6, wherein the displaying includes displaying first supplementary information attached to the false correspondence region by switching from a same manner as a manner of displaying second supplementary information attached to the non-false correspondence region to a different manner by a predetermined user operation.

8. The recording medium according to claim 1, wherein the instructions further cause the computer to execute:
    acquiring a lesion input region input by the user for the one or more first lesion detection regions obtained by the computer processing on the first medical image of the patient, and
    the displaying includes displaying a region that is obtained by excluding the false correspondence region from the one or more second lesion detection regions and that does not correspond to the lesion input region in a manner different from a manner of displaying the region corresponding to the lesion input region and the false correspondence region.

9. The recording medium according to claim 1, wherein the false correspondence region exists among the one or more second lesion detection regions, and
    the instructions further cause the computer to execute, in the displaying, at least one of:
        notifying the user of predetermined information,
        changing a manner of displaying a mouse cursor to be displayed, and
        changing a manner of displaying a window to be displayed.

10. The recording medium according to claim 1, wherein the displaying includes displaying the false correspondence region in a manner different from a manner of displaying the non-false correspondence region by highlighting first supplementary information attached to the false correspondence region.

11. The recording medium according to claim 1, wherein the first medical image is captured at date and time different from date and time of capturing the second medical image.

12. An information processing apparatus comprising a hardware processor that:
    acquires information on whether a first lesion detection region input by a user with respect to a first analysis result is false positive, wherein
        the first analysis result includes one or more first lesion detection regions obtained by computer processing on a first medical image of a patient;
    acquires a second analysis result including one or more second lesion detection regions that are obtained by computer processing on a second medical image of the patient; and
    among the one or more second lesion detection regions, displays a false correspondence region in a manner different from a manner of displaying a non-false correspondence region, wherein
        the false correspondence region corresponds to, among the one or more first lesion detection regions, a first lesion detection region indicated as being false positive in the acquired information, and
        the non-false correspondence region corresponds to, among the one or more first lesion detection regions, a first lesion detection region indicated as being not false positive in the acquired information.

13. The information processing apparatus according to claim 12, wherein the hardware processor displays first supplementary information attached to the false correspondence region and second supplementary information attached to the non-false correspondence region in different manners from each other.

14. The information processing apparatus according to claim 13, wherein the hardware processor displays the false correspondence region in a manner different from a manner of displaying the non-false correspondence region by hiding the first supplementary information attached to the false correspondence region.

15. The information processing apparatus according to claim 13, wherein the first supplementary information and the second supplementary information are annotation information.

16. The information processing apparatus according to claim 13, wherein the hardware processor displays the false correspondence region in a manner different from a manner of displaying the non-false correspondence region by displaying the first supplementary information attached to the false correspondence region and by refraining from displaying the second supplementary information attached to the non-false correspondence region.

17. The information processing apparatus according to claim 12, wherein the hardware processor displays the false correspondence region by switching from a same manner as a manner of displaying the non-false correspondence region to a different manner by a predetermined user operation.

18. The information processing apparatus according to claim 12, wherein the hardware processor displays first supplementary information attached to the false correspondence region by switching from a same manner as a manner of displaying second supplementary information attached to the non-false correspondence region to a different manner by a predetermined user operation.

19. The information processing apparatus according to claim 12, wherein
    the hardware processor:
        acquires a lesion input region input by the user for the one or more first lesion detection regions obtained by the computer processing on the first medical image of the patient, and
        displays a region that is obtained by excluding the false correspondence region from the one or more second lesion detection regions and that does not correspond to the lesion input region in a manner different from a manner of displaying the region corresponding to the lesion input region and the false correspondence region.

20. The information processing apparatus according to claim 12, wherein
    the false correspondence region exists among the one or more second lesion detection regions, and
    the hardware processor executes at least one of:
        notifying the user of predetermined information,
        changing a manner of displaying a mouse cursor to be displayed, and changing a manner of displaying a window to be displayed.

21. The information processing apparatus according to claim 12, wherein the hardware processor displays the false correspondence region in a manner different from a manner of displaying the non-false correspondence region by highlighting first supplementary information attached to the false correspondence region.

22. The information processing apparatus according to claim 12, wherein the first medical image is captured at date and time different from date and time of capturing the second medical image.

23. An information processing system comprising
a hardware processor that:
    acquires information on whether a first lesion detection region input by a user with respect to a first analysis result is false positive, wherein
    the first analysis result includes one or more first lesion detection regions obtained by computer processing on a first medical image of a patient;
    acquires a second analysis result including one or more second lesion detection regions that are obtained by computer processing on a second medical image of the patient; and
    among the one or more second lesion detection regions, displays a false correspondence region in a manner different from a manner of displaying a non-false correspondence region, wherein
    the false correspondence region corresponds to, among the one or more first lesion detection regions, a first lesion detection region indicated as being false positive in the acquired information, and
    the non-false correspondence region corresponds to, among the one or more first lesion detection regions, a first lesion detection region indicated as being not false positive in the acquired information.

24. An information processing method comprising:
acquiring information on whether a first lesion detection region input by a user with respect to a first analysis result is false positive, wherein
    the first analysis result includes one or more first lesion detection regions obtained by computer processing on a first medical image of a patient;
acquiring a second analysis result including one or more second lesion detection regions that are obtained by computer processing on a second medical image of the patient; and
among the one or more second lesion detection regions, displaying a false correspondence region in a manner different from a manner of displaying a non-false correspondence region, wherein
    the false correspondence region corresponds to, among the one or more first lesion detection regions, a first lesion detection region indicated as being false positive in the acquired information, and
    the non-false correspondence region corresponds to, among the one or more first lesion detection regions, a first lesion detection region indicated as being not false positive in the acquired information.

* * * * *